(12) United States Patent
Hert et al.

(10) Patent No.: US 10,889,588 B2
(45) Date of Patent: Jan. 12, 2021

(54) BICYCLIC COMPOUNDS AS DUAL ATX/CA INHIBITORS

(71) Applicant: Hoffmann-La Roche Inc., Little Falls, NJ (US)

(72) Inventors: Jerome Hert, Basel (CH); Daniel Hunziker, Basel (CH); Patrizio Mattei, Basel (CH); Markus Rudolph, Basel (CH); Petra Schmitz, Basel (CH); Christoph Ullmer, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/889,322

(22) Filed: Jun. 1, 2020

(65) Prior Publication Data

US 2020/0291038 A1    Sep. 17, 2020

Related U.S. Application Data

(60) Division of application No. 15/933,769, filed on Mar. 23, 2018, now Pat. No. 10,738,053, which is a continuation of application No. PCT/EP2016/072277, filed on Sep. 20, 2016.

(30) Foreign Application Priority Data

Sep. 24, 2015 (EP) .................................... 15186642

(51) Int. Cl.
| | | |
|---|---|---|
| C07D 487/04 | (2006.01) | |
| A61P 27/02 | (2006.01) | |
| A61K 31/407 | (2006.01) | |

(52) U.S. Cl.
CPC ............ *C07D 487/04* (2013.01); *A61P 27/02* (2018.01)

(58) Field of Classification Search
CPC ...... C07D 487/04; A61P 27/02; A61K 31/407
See application file for complete search history.

(56) References Cited

U.S. PATENT DOCUMENTS

| | | | |
|---|---|---|---|
| 5,202,322 A | 4/1993 | Allen et al. | |
| 5,238,942 A | 8/1993 | Chakravarty et al. | |
| 5,240,928 A | 8/1993 | Allen et al. | |
| 5,290,780 A | 3/1994 | Venkatesan et al. | |
| 5,304,565 A | 4/1994 | Morimoto et al. | |
| 5,358,951 A | 10/1994 | Levin et al. | |
| 5,470,975 A | 11/1995 | Atwal | |
| 5,472,961 A | 12/1995 | Gottschlich et al. | |
| 5,532,243 A | 7/1996 | Gilligan | |
| 6,821,964 B2 | 11/2004 | Colon-Cruz et al. | |
| 6,841,560 B2 | 1/2005 | Thompson et al. | |
| 7,271,260 B2 | 9/2007 | Lee et al. | |
| 8,329,907 B2 | 12/2012 | Schultz et al. | |
| 8,440,694 B2 | 5/2013 | Turner et al. | |
| 8,697,883 B2 | 4/2014 | Abouabdellah et al. | |
| 8,841,324 B2 | 9/2014 | Staehle et al. | |
| 8,946,264 B2 | 2/2015 | Shinozuka et al. | |
| 9,029,387 B2 | 5/2015 | Staehle et al. | |
| 9,493,486 B2 | 11/2016 | Hunziker et al. | |
| 9,580,434 B2 | 2/2017 | Mazurov et al. | |
| 9,598,418 B2 | 3/2017 | Srivastava et al. | |
| 9,802,944 B2 | 10/2017 | Di Giorgio et al. | |
| 10,208,052 B1 | 2/2019 | Zheng et al. | |
| 10,633,384 B2 | 4/2020 | Hunziker et al. | |
| 10,640,472 B2 | 5/2020 | Hert et al. | |
| 10,647,719 B2 | 5/2020 | Di Giorgio et al. | |
| 10,654,857 B2 | 5/2020 | Di Giorgio et al. | |
| 10,669,268 B2 | 6/2020 | Hert et al. | |
| 10,669,285 B2 | 6/2020 | Hunziker et al. | |
| 10,676,446 B2 | 6/2020 | Hert et al. | |
| 10,738,053 B2 | 8/2020 | Hert et al. | |
| 2005/0203112 A1 | 9/2005 | Castonguay et al. | |
| 2008/0090802 A1 | 4/2008 | Letourneau et al. | |
| 2010/0222341 A1 | 9/2010 | Schiemann et al. | |
| 2010/0298290 A1 | 11/2010 | Anand et al. | |
| 2011/0230471 A1 | 9/2011 | Staehle et al. | |
| 2012/0115852 A1 | 5/2012 | Schultz et al. | |

(Continued)

FOREIGN PATENT DOCUMENTS

| | | |
|---|---|---|
| CA | 2768095 | 1/2011 |
| CN | 1068114 A | 1/1993 |

(Continued)

OTHER PUBLICATIONS 959567-58-9,CAS Database Registry [retrieved online May 25, 2016] Chemical Abstracts Service Dec. 26, 2007 (Dec. 26, 2007, NIH Chemical Genomics Center: XP002707620, retrieved from STN Database accession No. 959567-58-9, pp. 1-2.
Albers et al., "Chemical Evolution of Autotaxin Inhibitors" Chemical Reviews (XP055073234), 112(5):2593-2603 (May 9, 2012).
Albers et al., "Discovery and Optimization of Boronic Acid Based Inhibitors of Autotaxin" 53(13):4958-4967 (Jul. 8, 2010).
Albers et al., "Structure-Based Design of Novel Boronic Acid-Based Inhibitors of Autotaxin" Journal of Medicinal Chemistry 54(13):4619-4626 ( 2011).
Anderson, "The Process of Structure-Based Drug Design" Chemistry & Biology 10:787-797 (Sep. 2003).
Angeli et al., "Synthesis and carbonic anhydrase inhibition of polycyclic imides moieties" Bioorgan Med Chem 25(20):5373-5379 (Oct. 20, 2017).

(Continued)

*Primary Examiner* — Amanda L. Aguirre
(74) *Attorney, Agent, or Firm* — Katherine J. Mackenzie

(57) ABSTRACT

The invention provides novel compounds having the general formula (I)

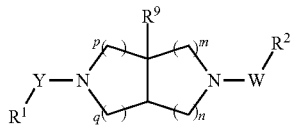

wherein $R^1$, $R^2$, $R^9$, Y, W, m, n, p and q are as defined herein, compositions including the compounds and methods of using the compounds.

23 Claims, No Drawings

(56) References Cited

U.S. PATENT DOCUMENTS

| | | | |
|---|---|---|---|
| 2015/0252046 A1* | 9/2015 | Staehle | A61P 9/00 514/307 |
| 2015/0353559 A1 | 12/2015 | Hert et al. | |
| 2015/0376194 A1 | 12/2015 | Hert et al. | |
| 2016/0264586 A1 | 9/2016 | Mattei et al. | |
| 2017/0008900 A1* | 1/2017 | Di Giorgio | C07D 487/04 |
| 2017/0050960 A1 | 2/2017 | Hert et al. | |
| 2018/0208602 A1* | 7/2018 | Di Giorgio | A61P 27/02 |
| 2018/0215765 A1* | 8/2018 | Di Giorgio | A61K 31/437 |
| 2018/0258095 A1 | 9/2018 | Hert et al. | |
| 2018/0280352 A1 | 10/2018 | Mattei et al. | |
| 2018/0312515 A1* | 11/2018 | Mattei | C07D 487/04 |
| 2018/0327410 A1* | 11/2018 | Grice | C07D 403/14 |
| 2018/0327416 A1* | 11/2018 | Grice | C07D 471/10 |
| 2019/0144457 A1* | 5/2019 | Di Giorgio | A61P 3/00 514/211.09 |
| 2020/0002297 A1 | 1/2020 | Mattei et al. | |
| 2020/0002336 A1 | 1/2020 | Hert et al. | |
| 2020/0079779 A1 | 3/2020 | Di Giorgio et al. | |
| 2020/0087307 A1 | 3/2020 | Mattei et al. | |
| 2020/0199155 A1 | 6/2020 | Hunziker et al. | |
| 2020/0207769 A1 | 7/2020 | Hunziker et al. | |
| 2020/0216457 A1 | 7/2020 | Di Giorgio et al. | |
| 2020/0223854 A1 | 7/2020 | Di Giorgio et al. | |

FOREIGN PATENT DOCUMENTS

| | | |
|---|---|---|
| CN | 1751047 A1 | 3/2006 |
| CN | 102459207 A | 5/2012 |
| CN | 103237799 A | 8/2013 |
| CN | 104428299 A | 3/2015 |
| CN | 104918917 A | 9/2015 |
| EP | 0417631 A2 | 3/1991 |
| EP | 0 424 850 A1 | 5/1991 |
| EP | 2301936 A1 | 3/2011 |
| EP | 3 187 492 A1 | 7/2017 |
| JP | 2001-039950 | 2/2001 |
| JP | 2005-239708 | 9/2005 |
| JP | 2007-176809 | 7/2007 |
| JP | 2008-501743 | 1/2008 |
| JP | 2008-031064 | 2/2008 |
| JP | 2008-031064 A | 2/2008 |
| JP | 2008-531533 | 8/2008 |
| JP | 2008-540547 | 11/2008 |
| JP | 2009-161449 | 7/2009 |
| KR | 2006-0088557 | 8/2006 |
| RU | 2375352 C2 | 12/2009 |
| RU | 2 480 463 | 4/2013 |
| RU | 2 483 068 | 5/2013 |
| RU | 2 517 693 | 5/2014 |
| WO | 99/40070 | 8/1999 |
| WO | 2001/030780 | 5/2001 |
| WO | 2002/070523 A1 | 9/2002 |
| WO | 2004/074291 A1 | 9/2004 |
| WO | 2005/023762 A1 | 3/2005 |
| WO | 2005/040167 A1 | 5/2005 |
| WO | 2005/058798 A2 | 6/2005 |
| WO | 2005/084667 | 9/2005 |
| WO | 2005/121145 | 12/2005 |
| WO | 2006/015985 A1 | 2/2006 |
| WO | 2006/077035 A1 | 7/2006 |
| WO | 2006/090143 | 8/2006 |
| WO | 2006/122137 | 11/2006 |
| WO | 2007/030061 A1 | 3/2007 |
| WO | 2007/058322 | 5/2007 |
| WO | 2007/103719 | 9/2007 |
| WO | 2008/033456 A1 | 3/2008 |
| WO | 2008/033764 A2 | 3/2008 |
| WO | 2008/059026 A1 | 5/2008 |
| WO | 2008/060767 A2 | 5/2008 |
| WO | 2008/076223 A1 | 6/2008 |
| WO | 2008/116881 A1 | 10/2008 |
| WO | 2008/119662 A1 | 10/2008 |
| WO | 2008/126034 | 10/2008 |
| WO | 2008/135141 A1 | 11/2008 |
| WO | 2007/049771 | 4/2009 |
| WO | 2009/046841 A2 | 4/2009 |
| WO | 2009/054914 A1 | 4/2009 |
| WO | 2009/058347 | 5/2009 |
| WO | 2009/154132 | 12/2009 |
| WO | 2010/028761 | 3/2010 |
| WO | 2010/051977 | 5/2010 |
| WO | 2010/055006 A1 | 5/2010 |
| WO | 2010/060532 A1 | 6/2010 |
| WO | 2010/063352 A1 | 6/2010 |
| WO | 2010/099938 | 9/2010 |
| WO | 2010/108268 | 9/2010 |
| WO | 2010/108651 | 9/2010 |
| WO | 2010/112116 A1 | 10/2010 |
| WO | 2010/112124 A1 | 10/2010 |
| WO | 2010/115491 A2 | 10/2010 |
| WO | 2010/130944 A1 | 11/2010 |
| WO | 2010/135524 | 11/2010 |
| WO | 2010/141817 A1 | 12/2010 |
| WO | 2011/006569 A1 | 1/2011 |
| WO | 2011-502150 | 1/2011 |
| WO | 2011/017350 | 2/2011 |
| WO | 2011/017561 | 2/2011 |
| WO | 2011/053948 | 5/2011 |
| WO | 2011/085170 | 7/2011 |
| WO | 2011/114271 A1 | 9/2011 |
| WO | 2011/115813 A1 | 9/2011 |
| WO | 2011/116867 A1 | 9/2011 |
| WO | 2011/141716 A2 | 11/2011 |
| WO | 2011/151461 A2 | 12/2011 |
| WO | 2012/020008 | 2/2012 |
| WO | 2012/024620 | 2/2012 |
| WO | 2012/028243 | 3/2012 |
| WO | 2012/080727 A1 | 6/2012 |
| WO | 2012/166415 | 12/2012 |
| WO | 2013/033059 A1 | 3/2013 |
| WO | 2013/054185 A1 | 4/2013 |
| WO | 2013/064467 A1 | 5/2013 |
| WO | 2013/079223 A1 | 6/2013 |
| WO | 2013/175053 | 11/2013 |
| WO | 2013/186159 A1 | 12/2013 |
| WO | 2014/007951 | 1/2014 |
| WO | 2014/018881 | 1/2014 |
| WO | 2014/018891 A1 | 1/2014 |
| WO | 2014/048865 A1 | 4/2014 |
| WO | 2014/048881 | 4/2014 |
| WO | 2014/055548 | 4/2014 |
| WO | 2014/066659 | 5/2014 |
| WO | 2014/102817 A1 | 7/2014 |
| WO | 2014/139324 | 9/2014 |
| WO | 2014/139978 A1 | 9/2014 |
| WO | 2014/143579 | 9/2014 |
| WO | 2014/152725 A1 | 9/2014 |
| WO | 2014/164905 | 10/2014 |
| WO | 2014/179564 | 11/2014 |
| WO | 2015/008230 A1 | 1/2015 |
| WO | 2013/065712 A1 | 4/2015 |
| WO | 2015/058031 | 4/2015 |
| WO | 2015/077503 A1 | 5/2015 |
| WO | 2015/078800 A1 | 6/2015 |
| WO | 2015/078803 | 6/2015 |
| WO | 2015/144480 A1 | 10/2015 |
| WO | 2015/144605 A1 | 10/2015 |
| WO | 2015/144609 A1 | 10/2015 |
| WO | 2015/144803 A1 | 10/2015 |
| WO | 2015/154023 A1 | 10/2015 |
| WO | 2016/061160 A1 | 4/2016 |
| WO | 2016/128529 A1 | 8/2016 |
| WO | 2016/162390 | 10/2016 |
| WO | 2014/133112 A1 | 2/2017 |
| WO | 2017/037146 | 3/2017 |
| WO | 2017/037670 A1 | 3/2017 |
| WO | 2017/050732 | 3/2017 |
| WO | 2017/050747 | 3/2017 |
| WO | 2017/050791 A1 | 3/2017 |
| WO | 2017/050792 A1 | 3/2017 |
| WO | 2016/031987 | 7/2017 |

(56) References Cited

FOREIGN PATENT DOCUMENTS

| WO | 2018/167001 A1 | 9/2018 |
| WO | 2018/167113 A1 | 9/2018 |
| WO | 3385261 A1 | 10/2018 |

OTHER PUBLICATIONS

Barbayianni et al., "Autotaxin inhibitors: a patent review" Expert Opin Ther Patents 23(9):1123-1132 ( 2013).
Benesch, Matthew G.K., et al., "Autotaxin in the crosshairs: Taking aim at cancer and other inflammatory conditions" FEBS LETT 588:2712-2727 (Feb. 19, 2014).
Bora, Rajesh O., et al., "[1, 2, 4]-Oxadiazoles: Synthesis and Biological Applications" Mini-Reviews in Med. Chem 14(4):355-369 (Mar. 13, 2014).
CAS Database Registry, ID#1206969-43-8 [retrieved online May 25, 2016], Feb. 22, 2010 (Feb. 22, 2010), BroadPharm:, retrieved from STN Database accession No. 1206969-43-8 the whole document.
CAS Registry Database, 1300725-30-7,Database Registry [retrieved online May 25, 2016] Chemical Abstracts Service May 25, 2011 (May 25, 2011), Focus Synthesis LLC: XP002707618, retrieved from STN Database accession No. 1300725-30-7 the whole document.
CAS Registry Database, 1352926-14-7,Database Registry [retrieved online May 25, 2016] Chemical Abstracts Service Jan. 12, 2012 (Jan. 12, 2012), All i chern LLC: XP002707617, retrieved from STN Database accession No. 1352926-14-7 see also RN: 135295-74-6; the whole document.
CAS Registry Database, 959567-58-9, ( ), pp. 1-38 Dec. 26, 2007.
Database Capulus (online) Chemical Abstracts Service Columbus Ohio, 1993, Database accession No. 1994:483155 RN156411-73-3, 156411-74-4 (1993).
Garcia-Gutierrez et al., "Novel inhibitors to Taenia solium Cu/Zn superoxide dismutase identified by virtual screening" J. Comp Aided Molecular Design 25:1135-1145 (2011).
Gierse et al., "A Novel Autotaxin Inhibitor Reduces Lysophosphatidic Acid Levels in Plasma and the Site of Inflammation" Pharmacol Exp Ther 334:310-317 ( 2010).
Henke, Brad R., et al., "Optimization of 3-(1H-Indazol-3-ylmethyl)-1,5-benzodiazepines as Potent, Orally Active CCK-A Agonists" J Med Chem 40:2706-2725 (Apr. 22, 1997).
Hoeglund et al., "Optimization of a pidemidic acid autotaxin inhibitor" Journal of Medicinal Chemistry 53:1056-1066 ( 2010).
"International Search Report—PCT/EP2014/054631":pp. 1-4 (dated Apr. 15, 2014).
"International Search Report—PCT/EP2014/075360":pp. 1-5 (dated Feb. 9, 2015).
"International Search Report—PCT/EP2015/056041":pp. 1-5 (dated May 6, 2015).
"International Search Report—PCT/EP2016/072277":pp. 1-5 (dated Dec. 8, 2016).
"International Search Report—PCT/EP2016/072349":pp. 1-5 (dated Nov. 29, 2016).
"International Search Report—PCT/EP2018/056140":pp. 1-9 (dated May 4, 2018).
"International Search Report—PCT/EP2018/056324":pp. 1-7 (dated May 8, 2018).
"International Search Report—PCT/EP2013/061890":pp. 1-9 (dated Sep. 17, 2013).
"International Search Report—PCT/EP2013/069679":pp. 1-3 (dated Nov. 8, 2013).
"International Search Report—PCT/EP2015/056032":pp. 1-5 (dated Apr. 23, 2015).
"International Search Report—PCT/EP2016/057549":pp. 1-5 (dated Jun. 22, 2016).
"International Search Report—PCT/EP2016/072243":pp. 1-5 (dated Dec. 6, 2016).
"International Search Report—PCT/EP2016/072347":pp. 1-5 (dated Jan. 17, 2017).
"International Search Report—PCT/EP2016/070561":pp. 1-6 (dated Oct. 28, 2016).
Jones et al., "Novel autotaxin inhibitors for the treatment of osteoarthritis pain: Lead optimization via structure-based drug design" ACS Med Chem Lett 7(9):857-861 ( 2016).
Kung et al., "Identification of spirocyclic piperidine-azetidine inverse agonists of the ghrelin receptor" Bioorg Med Chem Lett (XP028490993), 22:4281-4287 ( 2012).
Litherland et al., "The Amino-derivatives of Pentuerythritol. Part I. Preparation." J Chem Soc:1588-1595 (Jan. 1, 1938).
Liu, Medicinal Chemistry (English translation),:349 (Aug. 31, 2007).
Matralis et al., "Development and therapeutic potential of autotaxin small molecule inhibitors: From bench to advanced clinical trials" Med. Res. Rev.:1-38 ( 2018).
Orr et al., "One-pot synthesis of chiral azetidines from chloroaldehyde and chiral amines" Tetrahedron Lett 52:3618-3620 ( 2011).
Overberger et al., "Absolute Configuration of 2,7-Diazaspiro [4.4]nonane. A Reassignment" J. Org. Chem. 46:2757-2764 ( 1981).
Patani, G., et al., "Bioisosterism: A Rational Approach in Drug Design" Chem Rev 96(8):3147-3176 (Dec. 19, 1996).
Pouliot, Marie-France, et al., "Synthesis of 1,3,4-oxadiazoles from 1,2-diacylhydrazines using [Et2NSF2]BF4 as a practical cyclodehydration agent" Org. Biomol. Chem 10:988-993 (Oct. 27, 2012).
Sheridan et al., "The Most Common Chemical Replacements in Drug-Like Compounds" J. Chem. Inf. Comput. Sci. 42(1):103-108 ( 2002).
Sippy et al., "Preparation and characterization of N-(3-pyridinyl) spirocyclic diamines as ligands for nicotinic acetylcholine receptors" Bioorg Med Chem Lett 19:1682-1685 (2009).
STN Columbus (STN International), pp. 1-13 ( Oct. 9, 2015).
Stocks et al., "A Practical Method for Targeted Library Design Balancing Lead-like Properties with Diversity" Chem Med Chem (XP002707616), 4:800-808 ( 2009).
Tan, Pharmacology (English translation),:27-28 (Jul. 31, 2006).
Tucker, T., et al., "Discovery of 3-{5-[(6-Amino-1H-pyrazolo[3,4-b]pyridine-3-yl)methoxy]-2-chlorophenoxy}-5-chlorobenzonitrile (MK-4965): A Potent, Orally Bioavailable HIV-1 Non-Nucleoside Reverse Transcriptase Inhibitor with Improved Potency against Key Mutant Viruses" J Med Chem 51:6503-6511 (Jul. 11, 2008).
"U.S. Appl. No. 16/793,178, filed Feb. 18, 2020".
"U.S. Appl. No. 16/811,656, filed Mar. 6, 2020".
"U.S. Appl. No. 16/818,409, filed Mar. 13, 2020".
"U.S. Appl. No. 16/889,322, filed Jun. 1, 2020".

\* cited by examiner

BICYCLIC COMPOUNDS AS DUAL ATX/CA INHIBITORS

This application is a divisional of U.S. application Ser. No. 15/933,769, filed Mar. 23, 2018, which is a continuation of International Application No. PCT/EP2016/072277, filed Sep. 20, 2016, which claims priority to EP Application No. 15186642.3, filed Sep. 24, 2015, the disclosure of each of which is incorporated herein by reference in its entirety.

The present invention relates to organic compounds useful for therapy or prophylaxis in a mammal, and in particular to dual autotaxin (ATX)/carbonic anhydrase inhibitors which are inhibitors of lysophosphatidic acid (LPA) production and thus modulators of LPA levels and associated signaling, for the treatment or prophylaxis of inflammatory conditions, conditions of the nervous system, vascular and cardiovascular conditions, cancer, and ocular conditions.

The present invention provides novel compounds of formula (I)

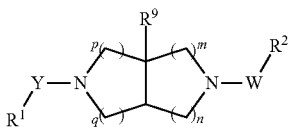

wherein
  $R^1$ is substituted phenyl, substituted phenyl-$C_{1-6}$-alkyl, substituted phenoxy-$C_{1-6}$-alkyl, substituted phenyl-$C_{2-6}$-alkenyl, substituted phenyl-$C_{2-6}$-alkynyl, substituted pyridinyl, substituted pyridinyl-$C_{1-6}$-alkyl, substituted pyridinyl-$C_{2-6}$-alkenyl, substituted pyridinyl-$C_{2-6}$-alkynyl, substituted thiophenyl, substituted thiophenyl-$C_{1-6}$-alkyl, substituted thiophenyl-$C_{2-6}$-alkenyl or substituted thiophenyl-$C_{2-6}$-alkynyl, wherein substituted phenyl, substituted phenyl-$C_{1-6}$-alkyl, substituted phenoxy-$C_{1-6}$-alkyl, substituted phenyl-$C_{2-6}$-alkenyl, substituted phenyl-$C_{2-6}$-alkynyl, substituted pyridinyl, substituted pyridinyl-$C_{1-6}$-alkyl, substituted pyridinyl-$C_{2-6}$-alkenyl, substituted pyridinyl-$C_{2-6}$-alkynyl, substituted thiophenyl, substituted thiophenyl-$C_{1-6}$-alkyl, substituted thiophenyl-$C_{2-6}$-alkenyl and substituted thiophenyl-$C_{2-6}$-alkynyl are substituted by $R^3$, $R^4$ and $R^5$;
  Y is —OC(O)— or —C(O)—;
  W is —C(O)—, —S(O)$_2$— or —CR$^6$R$^7$—;
  $R^2$ is substituted phenyl, substituted pyridinyl or substituted thiophenyl, wherein substituted phenyl, substituted pyridinyl and substituted thiophenyl are substituted by $R^6$, $R^7$ and $R^8$;
  $R^3$ is halogen, hydroxy, cyano, $C_{1-6}$-alkyl, $C_{1-6}$-alkoxy, $C_{1-6}$-alkoxy-$C_{1-6}$-alkyl, halo-$C_{1-6}$-alkoxy, halo-$C_{1-6}$-alkyl, hydroxy-$C_{1-6}$-alkyl, $C_{3-8}$-cycloalkyl, $C_{3-8}$-cycloalkyl-$C_{1-6}$-alkyl, $C_{3-8}$-cycloalkyl-$C_{1-6}$-alkoxy, $C_{3-8}$-cycloalkoxy, $C_{3-8}$-cycloalkoxy-$C_{1-6}$-alkyl, $C_{1-6}$-alkylamino, $C_{1-6}$-alkylcarbonylamino, $C_{3-8}$-cycloalkylcarbonylamino, $C_{1-6}$-alkyltetrazolyl, $C_{1-6}$-alkyltetrazolyl-$C_{1-6}$-alkyl or heterocycloalkyl-$C_{1-6}$-alkoxy;
  $R^4$ and $R^5$ are independently selected from H, halogen, hydroxy, cyano, $C_{1-6}$-alkyl, $C_{1-6}$-alkoxy, $C_{1-6}$-alkoxy-$C_{1-6}$-alkyl, halo-$C_{1-6}$-alkoxy, halo-$C_{1-6}$-alkyl, hydroxy-$C_{1-6}$-alkyl, $C_{3-8}$-cycloalkyl, $C_{3-8}$-cycloalkyl-$C_{1-6}$-alkyl, $C_{3-8}$-cycloalkyl-$C_{1-6}$-alkoxy, $C_{3-8}$-cycloalkoxy, $C_{3-8}$-cycloalkoxy-$C_{1-6}$-alkyl, $C_{1-6}$-alkylcarbonylamino, $C_{3-8}$-cycloalkylcarbonylamino, $C_{1-6}$-alkyltetrazolyl, $C_{1-6}$-alkyltetrazolyl-$C_{1-6}$-alkyl or heterocycloalkyl-$C_{1-6}$-alkoxy;
  $R^6$ is aminosulfonyl;
  $R^7$ and $R^8$ are independently selected from H, halogen, hydroxy, cyano, $C_{1-6}$-alkyl, $C_{1-6}$-alkoxy, $C_{1-6}$-alkoxy-$C_{1-6}$-alkyl, halo-$C_{1-6}$-alkoxy, halo-$C_{1-6}$-alkyl, hydroxy-$C_{1-6}$-alkyl, $C_{3-8}$-cycloalkyl, $C_{3-8}$-cycloalkyl-$C_{1-6}$-alkyl, $C_{3-8}$-cycloalkyl-$C_{1-6}$-alkoxy, $C_{3-8}$-cycloalkoxy and $C_{3-8}$-cycloalkoxy-$C_{1-6}$-alkyl;
  $R^9$ is $C_{1-6}$-alkyl, $C_{1-6}$-alkoxy or halogen;
  m, n, p and q are independently selected from 1 or 2;
  or pharmaceutically acceptable salts.

Autotaxin (ATX) is a secreted enzyme also called ecto-nucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1 (vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

Carbonic anhydrases (CA) are a family of zinc-dependent enzymes, which catalyze the equilibration between carbon dioxide and water and hydrogencarbonate and a proton. The CA reaction is involved in many physiological and pathological processes. Carbonic anhydrase inhibition is useful for the treatment of ocular conditions, conditions of reduced blood flow, cancer, edema and inflammatory conditions including bacterial infections.

Dual acting ATX/CA inhibitors are expected to lower intraocular pressure by facilitating two independent pathways, such as inhibition of aqueous humor (AH) production through CA inhibition at the ciliary body and facilitation of AH outflow by ATX inhibition within the AH drainage system. In conditions of vascular leakage in the eye such as diabetic retinopathy, age related macular disease, or retinal vein occlusion, CA levels have been shown or are expected to increase in the eye and facilitate an increase in pH. This is expected to activate many hydrolytic enzymes that can contribute to disease progression including ATX suggesting additional ATX inhibition by shifting the pH optimum.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and carbonic anhydrase activity therefore inhibit LPA production and modulate LPA levels and associated signaling. Dual ATX/CA-II inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and—chronic organ transplant rejection, and the use of the said compounds, salts or esters for the production of medicaments for the treatment or prophylaxis of inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particularly, the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

The term "$C_{1-6}$-alkoxy" denotes a group of the formula —O—R', wherein R' is an $C_{1-6}$-alkyl group. Examples of $C_{1-6}$-alkoxy group include methoxy, ethoxy, n-propoxy, isopropoxy, n-butoxy, isobutoxy and tert-butoxy. Particular example is methoxy.

The term "$C_{2-6}$-alkenyl" denotes a monovalent linear or branched hydrocarbon group of 2 to 6 carbon atoms with at least one double bond. Particular example is ethylenyl.

The term "$C_{1-6}$-alkoxy-$C_{1-6}$-alkyl" denotes a $C_{1-6}$-alkyl group wherein at least one of the hydrogen atoms of the $C_{1-6}$-alkyl group is replaced by a $C_{1-6}$-alkoxy group. Particular examples are methoxymethyl, methoxyethyl, ethoxymethyl, ethoxyethyl, iso-propoxymethyl and iso-propoxyethyl.

The term "$C_{1-6}$-alkyl" denotes a monovalent linear or branched saturated hydrocarbon group of 1 to 6 carbon atoms. Examples of $C_{1-6}$-alkyl include methyl, ethyl, propyl, isopropyl, n-butyl, iso-butyl, sec-butyl, tert-butyl and pentyl. Particular alkyl groups include methyl, ethyl, isopropyl, n-butyl and sec-butyl.

The term "$C_{1-6}$-alkylamino" a group of the formula —NH— R', wherein R' is an $C_{1-6}$-alkyl group. Particular $C_{1-6}$-alkylamino is a group of the formula —NH— R', wherein R' is ter-butyl.

The term "$C_{1-6}$-alkylcarbonylamino" denotes a group of the formula —NH—C(O)—R', wherein R' is an $C_{1-6}$-alkyl group. Particular $C_{1-6}$-alkylcarbonylamino is a group of the formula —NH—C(O)—R', wherein R' is ter-butyl.

The term "$C_{1-6}$-alkyltetrazolyl" denotes tetrazolyl group substituted with one $C_{1-6}$-alkyl group. Particular $C_{1-6}$-alkyltetrazolyl is methyltetrazolyl.

The term "$C_{1-6}$-alkyltetrazolyl-$C_{1-6}$-alkyl" denotes $C_{1-6}$-alkyl group wherein one of the hydrogen atoms of the $C_{1-6}$-alkyl group is replaced by a $C_{1-6}$-alkyltetrazolyl group. Particular example is methyltetrazolylmethyl.

The term "$C_{2-6}$-alkynyl" denotes a monovalent linear or branched hydrocarbon group of 2 to 6 carbon atoms with at least one triple bond.

The term "amino" denotes the —NH$_2$ group.

The term "aminosulfonyl" denotes —S(O)$_2$—NH$_2$ group.

The term "cyano" denotes a —C≡N group.

The term "$C_{3-8}$-cycloalkoxy" denotes a group of the formula —O—R', wherein R' is a $C_{3-8}$-cycloalkyl.

The term "$C_{3-8}$-cycloalkoxy-$C_{1-6}$-alkyl" denotes a $C_{1-6}$-alkyl group wherein at least one of the hydrogen atoms of the alkyl group is replaced by a $C_{3-8}$-cycloalkoxy group.

The term "$C_{3-8}$-cycloalkyl" denotes a monovalent saturated monocyclic or bicyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Examples for bicyclic $C_{3-8}$-cycloalkyl are bicyclo[2.2.1]heptanyl or bicyclo[2.2.2]octanyl. Particular $C_{3-8}$-cycloalkyl group is cyclopropyl.

The term "$C_{3-8}$-cycloalkyl-$C_{1-6}$-alkoxy" denotes a $C_{1-6}$-alkoxy group wherein at least one of the hydrogen atoms of the alkyl group is replaced by a $C_{3-8}$-cycloalkyl group.

The term "$C_{3-8}$-cycloalkyl-$C_{1-6}$-alkyl" denotes a $C_{1-6}$-alkyl group wherein at least one of the hydrogen atoms of the alkyl group is replaced by a $C_{3-8}$-cycloalkyl group.

The term "$C_{3-8}$-cycloalkylcarbonylamino" denotes a group of the formula —NH—C(O)—R', wherein R' is a $C_{3-8}$-cycloalkyl group.

The term "halo-$C_{1-6}$-alkoxy" denotes a $C_{1-6}$-alkoxy group wherein at least one of the hydrogen atoms of the alkoxy group has been replaced by the same or different halogen atoms. Particular examples are trifluoromethoxy.

The term "halogen" and "halo" are used interchangeably herein and denote fluoro, chloro, bromo or iodo. Particular halogens are chloro and fluoro.

The term "halo-$C_{1-6}$-alkyl" denotes a $C_{1-6}$-alkyl group wherein at least one of the hydrogen atoms of the $C_{1-6}$-alkyl group has been replaced by the same or different halogen atoms. Particular examples are trifluoromethyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydrooxazolyl, tetrahydro-pyridinyl, or dihydropyranyl. Particular example of heterocycloalkyl group is tetrahydropyranyl.

The term "heterocycloalkyl-$C_{1-6}$-alkoxy" denotes a $C_{1-6}$-alkoxy group wherein at least one of the hydrogen atoms of the alkyl group is replaced by a heterocycloalkyl group. Particular example of heterocycloalkyl-$C_{1-6}$-alkoxy is tetrahydropyranyl-$C_{1-6}$-alkoxy, more particularly tetrahydropyranylmethoxy.

The term "hydroxy" denotes a —OH group.

The term "hydroxy-$C_{1-6}$-alkyl" denotes a $C_{1-6}$-alkyl group wherein one of the hydrogen atoms of the alkyl group is replaced by a hydroxy group. Particular examples are hydroxymethyl and hydroxyethyl.

The term "phenoxy" denotes a group of the formula —O—R', wherein R' is a phenyl group.

The term "phenoxy-$C_{1-6}$-alkyl" denotes a $C_{1-6}$-alkyl group wherein one of the hydrogen atoms of the alkyl group is replaced by a phenoxy group.

The term "phenyl-$C_{2-6}$-alkenyl" denotes a $C_{2-6}$-alkenyl group wherein one of the hydrogen atoms of the alkyl group is replaced by a phenyl group. Particular example of phenyl-$C_{2-6}$-alkenyl is phenylethenyl.

The term "phenyl-$C_{1-6}$-alkyl" denotes a $C_{1-6}$-alkyl group wherein one of the hydrogen atoms of the alkyl group is replaced by a phenyl group. Particular examples of phenyl-$C_{1-6}$-alkyl are phenylmethyl and phenylethyl.

The term "phenyl-$C_{2-6}$-alkynyl" denotes a $C_{2-6}$-alkynyl group wherein one of the hydrogen atoms of the alkyl group is replaced by a phenyl group.

The term "pyridinyl-$C_{2-6}$-alkenyl" denotes a $C_{2-6}$-alkenyl group wherein one of the hydrogen atoms of the alkyl group is replaced by a pyridinyl group.

The term "pyridinyl-$C_{1-6}$-alkyl" denotes a $C_{1-6}$-alkyl group wherein one of the hydrogen atoms of the alkyl group is replaced by a pyridinyl group. Particular example of pyridinyl-$C_{1-6}$-alkyl is pyridinylmethyl, more particularly 2-pyridinylmethyl.

The term "pyridinyl-$C_{2-6}$-alkynyl" denotes a $C_{2-6}$-alkynyl group wherein one of the hydrogen atoms of the alkyl group is replaced by a pyridinyl group.

The term "thiophenyl-$C_{2-6}$-alkenyl" denotes a $C_{2-6}$-alkenyl group wherein one of the hydrogen atoms of the alkyl group is replaced by a thiophenyl group.

The term "thiophenyl-$C_{1-6}$-alkyl" denotes a $C_{1-6}$-alkyl group wherein one of the hydrogen atoms of the alkyl group is replaced by a thiophenyl group.

The term "thiophenyl-$C_{2-6}$-alkynyl" denotes a $C_{2-6}$-alkynyl group wherein one of the hydrogen atoms of the alkyl group is replaced by a thiophenyl group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein
$R^1$ is substituted phenyl-$C_{1-6}$-alkyl, substituted phenoxy-$C_{1-6}$-alkyl, substituted phenyl-$C_{2-6}$-alkenyl, substituted pyridinyl or substituted pyridinyl-$C_{1-6}$-alkyl, wherein substituted phenyl-$C_{1-6}$-alkyl, substituted phenoxy-$C_{1-6}$-alkyl, substituted phenyl-$C_{2-6}$-alkenyl, substituted pyridinyl and substituted pyridinyl-$C_{1-6}$-alkyl are substituted by $R^3$, $R^4$ and $R^5$;
Y is a —OC(O)— or —C(O)—;
W is —C(O)—;
$R^2$ is substituted phenyl or substituted pyridinyl, wherein substituted phenyl and substituted pyridinyl are substituted by $R^6$, $R^7$ and $R^8$;
$R^3$ is halo-$C_{1-6}$-alkoxy, $C_{1-6}$-alkylcarbonylamino or tetrahydropyranyl-$C_{1-6}$-alkoxy;
$R^4$ is H, $C_{1-6}$-alkyl or $C_{3-8}$-cycloalkyl;
$R^5$ is H;
$R^6$ is aminosulfonyl;
$R^7$ and $R^8$ are independently selected from H and halogen;
$R^9$ is $C_{1-6}$-alkyl, $C_{1-6}$-alkoxy or halogen;
m, n, p and q are 1;
or pharmaceutically acceptable salts.

A particular embodiment of the present invention are compounds according to formula (I) as described herein, wherein $R^1$ is substituted phenyl-$C_{1-6}$-alkyl, substituted phenoxy-$C_{1-6}$-alkyl, substituted phenyl-$C_{2-6}$-alkenyl, substituted pyridinyl or substituted pyridinyl-$C_{1-6}$-alkyl, wherein substituted phenyl-$C_{1-6}$-alkyl, substituted phenoxy-$C_{1-6}$-alkyl, substituted phenyl-$C_{2-6}$-alkenyl, substituted pyridinyl and substituted pyridinyl-$C_{1-6}$-alkyl are substituted by $R^3$, $R^4$ and $R^5$.

A further particular embodiment of the present invention are compounds according to formula (I) as described herein, wherein $R^1$ is substituted pyridinyl or substituted pyridinyl-$C_{1-6}$-alkyl, wherein substituted pyridinyl and substituted pyridinyl-$C_{1-6}$-alkyl are substituted by $R^3$, $R^4$ and $R^5$.

A particular embodiment of the present invention are compounds according to formula (I) as described herein, wherein Y is —C(O)—.

A particular embodiment of the present invention are compounds according to formula (I) as described herein, wherein $R^2$ is substituted phenyl or substituted pyridinyl, wherein substituted phenyl and substituted pyridinyl are substituted by $R^6$, $R^7$ and $R^8$.

A particular embodiment of the present invention are compounds according to formula (I) as described herein, wherein $R^3$ is halo-$C_{1-6}$-alkoxy, $C_{1-6}$-alkylcarbonylamino or tetrahydropyranyl-$C_{1-6}$-alkoxy.

A further particular embodiment of the present invention are compounds according to formula (I) as described herein, wherein $R^3$ is tetrahydropyranyl-$C_{1-6}$-alkoxy.

A particular embodiment of the present invention are compounds according to formula (I) as described herein, wherein $R^4$ is H, $C_{1-6}$-alkyl or $C_{3-8}$-cycloalkyl.

A further particular embodiment of the present invention are compounds according to formula (I) as described herein, wherein $R^4$ is $C_{3-8}$-cycloalkyl.

A particular embodiment of the present invention are compounds according to formula (I) as described herein, wherein $R^5$ is H.

A particular embodiment of the present invention are compounds according to formula (I) as described herein, wherein $R^7$ and $R^8$ are independently selected from H and halogen.

A further particular embodiment of the present invention are compounds according to formula (I) as described herein, wherein $R^7$ is H or halogen.

A further particular embodiment of the present invention are compounds according to formula (I) as described herein, wherein $R^8$ is H.

A particular embodiment of the present invention are compounds according to formula (I) as described herein, wherein $R^9$ is halogen or $C_{1-6}$-alkoxy.

A particular embodiment of the present invention are compounds according to formula (I) as described herein, wherein m, n, p and q are 1.

A more particular embodiment of the present invention are compounds according to formula (I) as described herein, wherein
$R^1$ is substituted pyridinyl or substituted pyridinyl-$C_{1-6}$-alkyl, wherein substituted pyridinyl and substituted pyridinyl-$C_{1-6}$-alkyl are substituted by $R^3$, $R^4$ and $R^5$;
Y is —C(O)—;
W is —C(O)—;
$R^2$ is substituted phenyl or substituted pyridinyl, wherein substituted phenyl and substituted pyridinyl are substituted by $R^6$, $R^7$ and $R^8$;
$R^3$ is tetrahydropyranyl-$C_{1-6}$-alkoxy;
$R^4$ is $C_{3-8}$-cycloalkyl;
$R^5$ is H;
$R^6$ is aminosulfonyl;
$R^7$ is H or halogen;
$R^8$ is H;
$R^9$ is halogen or $C_{1-6}$-alkoxy;
m, n, p and q are 1
or pharmaceutically acceptable salts.

A particular embodiment of the present invention are compounds according to formula I(a) as described herein,

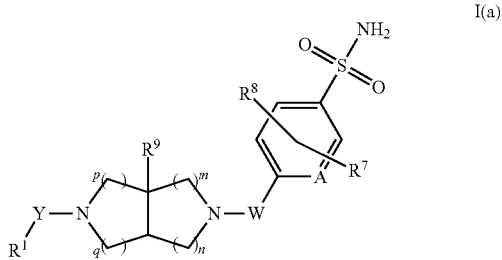

wherein
$R^1$ is substituted phenyl-$C_{1-6}$-alkyl, substituted phenoxy-$C_{1-6}$-alkyl, substituted phenyl-$C_{2-6}$-alkenyl, substituted pyridinyl or substituted pyridinyl-$C_{1-6}$-alkyl, wherein substituted phenyl-$C_{1-6}$-alkyl, substituted phenoxy-$C_{1-6}$-alkyl, substituted phenyl-$C_{2-6}$-alkenyl, substituted pyridinyl and substituted pyridinyl-$C_{1-6}$-alkyl are substituted by $R^3$, $R^4$ and $R^5$;
Y is a —OC(O)— or —C(O)—;

W is —C(O)—;
R² is substituted phenyl or substituted pyridinyl, wherein substituted phenyl and substituted pyridinyl are substituted by R⁶, R⁷ and R⁸;
R³ is halo-$C_{1-6}$-alkoxy, $C_{1-6}$-alkylcarbonylamino or tetrahydropyranyl-$C_{1-6}$-alkoxy;
R⁴ is H, $C_{1-6}$-alkyl or $C_{3-8}$-cycloalkyl;
R⁵ is H;
R⁷ and R⁸ are independently selected from H and halogen;
R⁹ is $C_{1-6}$-alkyl, $C_{1-6}$-alkoxy or halogen;
m, n, p and q are 1;
or pharmaceutically acceptable salts.

A further particular embodiment of the present invention are compounds according to formula I(b) as described herein,

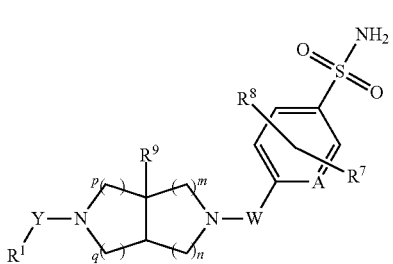

wherein
R¹ is substituted pyridinyl or substituted pyridinyl-$C_{1-6}$-alkyl, wherein substituted pyridinyl and substituted pyridinyl-$C_{1-6}$-alkyl are substituted by R³, R⁴ and R⁵;
Y is —C(O)—;
W is —C(O)—;
R² is substituted phenyl or substituted pyridinyl, wherein substituted phenyl and substituted pyridinyl are substituted by R⁶, R⁷ and R⁸;
R³ is tetrahydropyranyl-$C_{1-6}$-alkoxy;
R⁴ is $C_{3-8}$-cycloalkyl;
R⁵ is H;
R⁷ is H or halogen;
R⁸ is H;
R⁹ is halogen or $C_{1-6}$-alkoxy;
m, n, p and q are 1
or pharmaceutically acceptable salts.

Particular examples of compounds of formula (I) as described herein are selected from
trans-5-(2-fluoro-4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;
trans-4-[3a-methoxy-2-[3-[4-(trifluoromethoxy)phenyl]propanoyl]-3,4,6,6a-tetrahydro-1H-pyrrolo[3,4-c]pyrrole-5-carbonyl]-3-fluorobenzenesulfonamide;
trans-4-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]-3-fluorobenzenesulfonamide;
trans-5-(4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;
trans-5-(4-sulfamoyl-benzoyl)-3a-fluoro-hexahydro-pyrrolo[3,4-c]pyrrole-2-carboxylic acid 4-trifluoromethoxy-benzyl ester;
trans-5-(4-sulfamoyl-benzoyl)-3a-methoxy-hexahydro-pyrrolo[3,4-c]pyrrole-2-carboxylic acid 4-trifluoromethoxy-benzyl ester;
trans-3a-methyl-5-(4-sulfamoyl-benzoyl)-hexahydro-pyrrolo[3,4-c]pyrrole-2-carboxylic acid 4-trifluoromethoxy-benzyl ester;
trans-5-(5-sulfamoylpyridine-2-carbonyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;
trans-6-[3a-methoxy-2-[3-[4-(trifluoromethoxy)phenyl]propanoyl]-3,4,6,6a-tetrahydro-1H-pyrrolo[3,4-c]pyrrole-5-carbonyl]pyridine-3-sulfonamide;
trans-6-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]pyridine-3-sulfonamide;
trans-5-(2-fluoro-4-sulfamoyl-benzoyl)-3a-fluoro-hexahydro-pyrrolo[3,4-c]pyrrole-2-carboxylic acid 4-trifluoromethoxy-benzyl ester;
trans-4-[3a-fluoro-2-[(E)-3-[4-(trifluoromethoxy)phenyl]prop-2-enoyl]-3,4,6,6a-tetrahydro-1H-pyrrolo[3,4-c]pyrrole-5-carbonyl]-3-fluorobenzenesulfonamide;
trans-4-[3a-fluoro-2-[2-[4-(trifluoromethoxy)phenoxy]acetyl]-3,4,6,6a-tetrahydro-1H-pyrrolo[3,4-c]pyrrole-5-carbonyl]-3-fluorobenzenesulfonamide;
trans-4-[5-[2-cyclopropyl-6-(oxan-4-ylmethoxy)pyridine-4-carbonyl]-3a-fluoro-3,4,6,6a-tetrahydro-1H-pyrrolo[3,4-c]pyrrole-2-carbonyl]-3-fluorobenzenesulfonamide;
trans-4-[3a-fluoro-2-[3-[4-(trifluoromethoxy)phenyl]propanoyl]-3,4,6,6a-tetrahydro-1H-pyrrolo[3,4-c]pyrrole-5-carbonyl]-3-fluorobenzenesulfonamide;
(+)-(3aR,6aR)-3a-methyl-5-(4-sulfamoyl-benzoyl)-hexahydro-pyrrolo[3,4-c]pyrrole-2-carboxylic acid 4-trifluoromethoxy-benzyl ester;
(−)-trans-5-(4-sulfamoyl-benzoyl)-3a-methoxy-hexahydro-pyrrolo[3,4-c]pyrrole-2-carboxylic acid 4-trifluoromethoxy-benzyl ester;
(−)-trans-5-(4-sulfamoyl-benzoyl)-3a-fluoro-hexahydro-pyrrolo[3,4-c]pyrrole-2-carboxylic acid 4-trifluoromethoxy-benzyl ester;
(−)-trans-5-(4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;
(−)-(3aS,6aS)-3a-methyl-5-(4-sulfamoylbenzoyl)-hexahydro-pyrrolo[3,4-c]pyrrole-2-carboxylic acid 4-trifluoromethoxy-benzyl ester;
(+)-trans-5-(4-sulfamoyl-benzoyl)-3a-methoxy-hexahydro-pyrrolo[3,4-c]pyrrole-2-carboxylic acid 4-trifluoromethoxy-benzyl ester;
(+)-trans-5-(4-sulfamoyl-benzoyl)-3a-fluoro-hexahydro-pyrrolo[3,4-c]pyrrole-2-carboxylic acid 4-trifluoromethoxy-benzyl ester;
(+)-trans-5-(4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;
and pharmaceutically acceptable salts thereof.

Further particular examples of compounds of formula (I) as described herein are selected from
trans-4-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]-3-fluorobenzenesulfonamide;
trans-6-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]pyridine-3-sulfonamide;
trans-4-[5-[2-cyclopropyl-6-(oxan-4-ylmethoxy)pyridine-4-carbonyl]-3a-fluoro-3,4,6,6a-tetrahydro-1H-pyrrolo[3,4-c]pyrrole-2-carbonyl]-3-fluorobenzenesulfonamide;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

Compounds of general formula (I) can be synthesised from amine precursor 1 and appropriate reagents, using methods well known in the art.

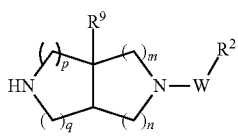

1

For instance, amine 1 is reacted with a suitable carboxylic acid of formula $R^1$—COOH (2) leading to a compound of formula (I), wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 1 can also be reacted with suitable acylating reagents such as acyl chlorides of formula $R^1$—COCl (3) to lead to compounds of formula (I), wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 1 is reacted with a suitable chloroformate ester of formula $R^1$—O—C(O)—Cl (4), or with an imidazole-1-carboxylate ester of formula (3), leading to a compound of formula (I) wherein Y is —OC(O)—.

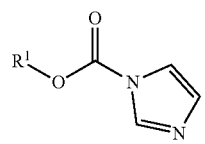

5

The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Chloroformate esters 4 are commercially available or can be synthesised from the corresponding alcohol of formula $R^1$—OH, by reaction with phosgene or a phosgene equivalent (e. g., diphosgene, triphosgene), as described in the literature.

Imidazole-1-carboxylate esters 5 are synthesised from the corresponding alcohols of formula $R^1$—OH, by reaction with 1,1'-carbonyldiimidazole. The reaction is performed at room temperature, in a solvent such as dichloromethane, tetrahydrofuran or acetonitrile. The imidazole-1-carboxylate esters 5 are typically not isolated but directly reacted with amines 1 as described above.

Alcohols of formula $R^1$—OH are commercially available or can be produced by methods described herein or known in the art.

Carboxylic acids (2) and acyl halides (3) are commercially available or can be prepared as described herein or in the literature.

Amines of general formula 1 are synthesised from suitably protected precursors 6.

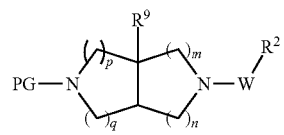

6

Suitable protective groups (PG) are tert-butoxycarbonyl or benzyloxycarbonyl. The deprotection of intermediates 6 can be performed using methods and reagents known in the art.

For instance, in the case where PG is benzyloxycarbonyl, the deprotection may be performed by hydrogenation at pressures between 1 bar and 100 bar, in the presence of a suitable catalyst such as palladium on activated charcoal, at temperatures between 20° C. and 150° C. in solvents such as methanol or ethanol.

Alternatively, in the case where PG is tert-butoxycarbonyl, the deprotection may be performed in the presence of a suitable acid, e. g, hydrochloric acid or trifluoroacetic acid, in a solvent such as water, 2-propanol, dichloromethane, or 1,4-dioxane at temperatures between 0° C. and 30° C.

Intermediates 6 can be produced from amine precursors of general formula 7 by reaction with appropriate reagents, using methods known in the art.

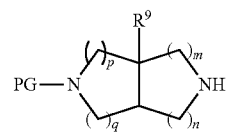

7

For instance, 7 is reacted with alkylating agents of general formula X—$CR^7R^8$—$R^2$ (8) where X is a leaving group such as Cl, Br, I, or $OSO_2CH_3$, leading to 6, wherein W is —$CR^7R^8$—. This reaction is performed in a solvent such as tetrahydrofuran or N,N-dimethylformamide, in the presence of a base, e. g. triethylamine or potassium carbonate, at temperatures between 0° C. and 100° C.

Alternatively, for compounds of formula 6, wherein W is —$CR^7R^8$—, $R^7$ is hydrogen, alkyl or cycloalkyl, and $R^8$ is H, amine 7 is reacted with aldehydes or ketones of general formula $R^7$—C(O)—$R^2$ (9) in a reductive amination reaction, leading to 6. This reaction is performed in the presence of a suitable reducing agent, e. g., sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 7 is reacted with a suitable carboxylic acid of formula $R^2$—COOH (10), leading to compounds of formula 6, wherein W is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, amine 7 is reacted with a suitable sulfonyl chloride of formula $R^2$—$SO_2Cl$ (11), leading to compounds of formula 6, wherein W is —$S(O_2)$—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Amines 7, alkylating agents 8, aldehydes/ketones 9, carboxylic acids 10, and sulfonyl chlorides 11 are commercially available or can be synthesised as described herein or in the literature.

Compounds of formula (I), can be produced from amine precursors of general formula 12 by reaction with appropriate reagents, using methods known in the art.

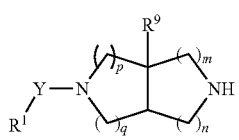

12

For instance, an amine of formula 12 is reacted with alkylating agents of general formula X—$CR^7R^8$—$R^2$ (8) where X is a leaving group such as Cl, Br, I, or $OSO_2CH_3$, leading to compounds of formula (I), wherein W is —$CR^7R^8$—. This reaction is performed in a solvent such as tetrahydrofuran or N,N-dimethylformamide, in the presence of a base, e. g., triethylamine or potassium carbonate, at temperatures between 0° C. and 100° C.

Alternatively, an amine of formula 12 is reacted with aldehydes or ketones of general formula $R^7$—C(O)—$R^2$ (9) in a reductive amination reaction, leading to compounds of formula (I) wherein W is —$CR^7R^8$—, $R^7$ is hydrogen, alkyl or cycloalkyl, and $R^8$ is H. This reaction is performed in the presence of a suitable reducing agent, e. g. sodium borohydride or sodium triacetoxyborohydride, in a solvent such as methanol, acetic acid, tetrahydrofuran, 1,2-dichloroethane or mixtures thereof, at temperatures between 0° C. and 50° C.

Alternatively, amine 12 is reacted with a suitable carboxylic acid of formula $R^2$—COOH (10), leading to compounds of formula (I) wherein W is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Alternatively, amine 12 is reacted with a suitable sulfonyl chloride of formula $R^2$—$SO_2Cl$ (11), leading to (I) wherein W is —$S(O_2)$—. The reaction is performed in a suitable solvent such as dichloromethane, tetrahydrofuran, N,N-dimethylformamide, acetonitrile, acetone, water, or mixtures thereof, in the presence of a base, e. g. triethylamine, diisopropylethylamine, pyridine, potassium hydrogencarbonate, potassium carbonate, at temperatures between 0° C. and the boiling point of the solvent or solvent mixture.

Amines 12 can be synthesised from their tert-butyl carbamate derivatives of formula 13 by carbamate deprotection. The deprotection may be performed in the presence of a suitable acid, e. g., hydrochloric acid or trifluoroacetic acid, in a solvent such as water, 2-propanol, dichloromethane, or 1,4-dioxane, at temperatures between 0° C. and 30° C.

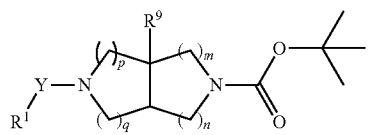

13 tert-Butyl carbamates 13 can be synthesised from amine precursors of formula 14 and appropriate reagents, using methods well known in the art.

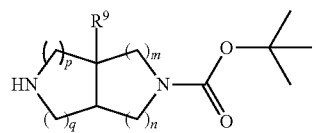

14

For instance, amine 14 is reacted with a suitable carboxylic acid of formula $R^1$—COOH (2) leading to compounds of formula 13, wherein Y is —C(O)—. The reaction is performed in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N, N,N',N'-tetramethyluronium hexafluoro-phosphate or bromo-tris-pyrrolidino-phosphonium hexafluorophosphate, in aprotic solvents such as dichloromethane, tetrahydrofuran, N,N-dimethylformamide, N-methylpyrrolidinone and mixtures thereof at temperatures between −40° C. and 80° C. in the presence or absence of a base such as triethylamine, diisopropylethylamine, 4-methylmorpholine and/or 4-(dimethylamino)pyridine.

Amine 14 can also be reacted with suitable acylating reagents, such as acyl chlorides of formula $R^1$—COCl (3) to provide compounds of formula 13, wherein Y is —C(O)—. The reaction is performed in a solvent such as dichloromethane, tetrahydrofuran, or N,N-dimethylformamide, in the presence of a base such as triethylamine or 4-methylmorpholine, at temperatures between 0° C. and 80° C.

Alternatively, amine 14 is reacted with a suitable chloroformate ester of formula $R^1$—O—C(O)—Cl (4), or with an imidazole-1-carboxylate ester of formula 5, leading to a compound of formula 13, wherein Y is —OC(O)—. The reaction is performed in a suitable solvent such as dichloromethane, tetrahydrofuran, N,N-dimethylformamide, acetonitrile, acetone, water, or mixtures thereof, in the presence of a base, e. g., triethylamine, diisopropylethylamine, pyridine, potassium hydrogencarbonate, potassium carbonate, at temperatures between 0° C. and the boiling point of the solvent or solvent mixture.

Alternatively, amine 14 can be reacted with a phosgene or a phosgene equivalent (e. g., triphosgene) to the corresponding N-chlorocarbonylamine 14A, in the presence of a base (e. g., pyridine) in a suitable solvent, e. g., dichloromethane, at temperatures between −78° C. and +20° C. N-Chlorocarbonylamine 14A is then reacted with alcohol of formula $R^1$—OH, leading to a compound of formula 13, wherein Y is —OC(O)—. This reaction is performed in a suitable solvent (e. g., acetonitrile of dichloromethane) in the presence of a suitable base (e. g., sodium hydride, pyridine or polystyrene-bound 2-tert-butylimino-2-diethylamino-1,3-dimethylperhydro-1,3,2-diazaphosphorine), at temperatures between 20° C. and the boiling point of the solvent.

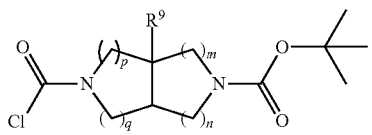

14A

Amines of formula 22 are commercially available or can be produced as described herein or in the literature.

Also an embodiment of the present invention is a process to prepare a compound of formula (I) as defined above comprising the reaction of a compound of formula (II) in the presence of a compound of formula (III);

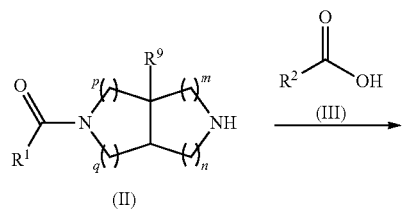

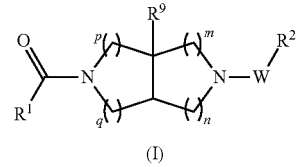

(I)

wherein $R^1$, $R^2$, $R^9$, m, n, p and q are as defined above and W is —C(O)—.

In particular, in the presence of a coupling agent such as 1,1'-carbonyldiimidazole, N,N'-dicyclohexylcarbodiimide, 1-(3-dimethylaminopropyl)-3-ethyl-carbodiimide hydrochloride, O-(benzotriazol-1-yl)-N,N,N',N'-tetramethyluronium hexafluoro-phosphate, O-(7-azabenzotriazol-1-yl)-N,N,N',N'-tetramethyluronium hexafluoro-phosphate or bromo-tris-pyrrolidino-phosphonium hexafluorophosphate, particularly O-(7-azabenzotriazol-1-yl)-N,N,N',N'-tetramethyluronium hexafluoro-phosphate, in an aprotic solvent such as dichloromethane, tetrahydrofuran, N,N-dimethylformamide, N-methylpyrrolidinone and mixtures thereof, particularly N,N-dimethylformamide, in the presence or absence of a base such as triethylamine, diisopropylethylamine, 4-methylmorpholine and/or 4-(dimethylamino)pyridine, particularly in the presence of 4-methylmorpholine and at a temperature comprised between −78° C. and reflux, particularly between −10° C. and room temperature.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A particular embodiment of the present invention is a compound according to formula (I) as described herein for the treatment or prophylaxis of ocular conditions, particularly glaucoma.

The present invention also relates to the use of a compound according to formula (I) as described herein for the preparation of a medicament for the treatment or prophylaxis of ocular conditions, particularly glaucoma.

Also an object of the invention is a method for the treatment or prophylaxis of ocular conditions, particularly glaucoma, which method comprises administering an effective amount of a compound according to formula (I) as described herein.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

Also an embodiment of the present invention are compounds of formula (I) as described herein, when manufactured according to any one of the described processes.

Assay Procedures
Production of Human Full Length ATX, with and without His Tag
Autotaxin (ATX-ENPP2) Cloning:

cDNA was prepared from commercial human hematopoietic cells total RNA and used as template in overlapping PCR to generate a full length human ENPP2 ORF with or without a 3'-6×His tag. These full length inserts were cloned into the pcDNA3.1V5-His TOPO (Invitrogen) vector. The DNA sequences of several single clones were verified. The DNA from a correct full length clone was used to transfect Hek293 cells for verification of protein expression. The sequence of the encoded ENPP2 conforms to Swissprot entry Q13822, with or without the additional C-terminal 6×His tag.

ATX Fermentation:

Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification:

20 liter of culture supernatant were conditioned for ultrafiltration by adding Brij 35 to a final concentration of 0.02% and by adjusting the pH to 7.0 using 1 M HCl. Then the supernatant was first microfiltred through a 0.2 □m Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, $NiSO_4$ was added to a final concentration of 1 mM. The cleared supernatant was then applied to a HisTrap column (GE Healthcare) previously equilibrated in 50 mM $Na_2HPO_4$ pH 7.0, 0.5 M NaCl, 10% glycerol, 0.3% CHAPS, 0.02% $NaN_3$. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% $NaN_3$. Final yield of protein after purification was 5-10 mg ATX per liter of culture supernatant. The protein was stored at −80° C.

Human ATX Enzyme Inhibition Assay

ATX inhibition was measured by a fluorescence quenching assay using a specifically labeled substrate analogue (MR121 substrate). To obtain this MR121 substrate, BOC and TBS protected 6-amino-hexanoic acid (R)-3-({2-[3-(2-{2-[2-(2-amino-ethoxy)-ethoxy]-ethoxy}-ethoxy)-propionylamino]-ethoxy}-hydroxy-phosphoryloxy)-2-hydroxy-propyl ester (Ferguson et al., Org Lett 2006, 8 (10), 2023) was labeled with MR121 fluorophore (CAS 185308-24-1, 1-(3-carboxypropyl)-11-ethyl-1,2,3,4,8,9,10,11-octahydro-dipyrido[3,2-b:2',3'-i]phenoxazin-13-ium) on the free amine of the ethanolamine side and then, after deprotection, subsequently with tryptophan on the side of the aminohexanoic acid.

Assay working solutions were made as follows:
Assay buffer (50 mM Tris-HCl, 140 mM NaCl, 5 mM KCl, 1 mM $CaCl_2$, 1 mM $MgCl_2$, 0.01% Triton-X-100, pH 8.0;
ATX solution: ATX (human His-tagged) stock solution (1.08 mg/mL in 20 mM bicine, pH 8.5, 0.15 M NaCl, 10% glycerol, 0.3% CHAPS, 0.02% $NaN_3$), diluted to 1.4-2.5× final concentration in assay buffer;
MR121 substrate solution: MR121 substrate stock solution (800 μM MR121 substrate in DMSO), diluted to 2-5× final concentration in assay buffer.

Test compounds (10 mM stock in DMSO, 8 μL) were obtained in 384 well sample plates (Corning Costar #3655) and diluted with 8 μL DMSO. Row-wise serial dilutions were made by transferring 8 μL cpd solution to the next row up to row O. The compound and control solutions were mixed five times and 2 μL were transferred to 384 well assay plates (Corning Costar #3702). Then, 15 μL of 41.7 nM ATX solution was added (30 nM final concentration), mixed five times and then incubated for 15 minutes at 30° C. 10 μL of MR121 substrate solution was added (1 μM final concentration), mixed 30 times and then incubated for 15 minutes at 30° C. Fluorescence was then measured every 2 minutes for 1 hour (Perkin Elmer plate: vision multimode reader); light intensity: 2.5%; exp. time: 1.4 sec, Filter: Fluo_630/690 nm) and $IC_{50}$ values were calculated from these readouts.

Human Carbonic Anhydrase-II Inhibition Assay

Human carbonic anhydrase II (hCA-II) inhibition was measured by an absorbance method using 4-nitrophenyl acetate (4-NPA) as its substrate. 4-NPA can be catalyzed by active hCA II via a zinc-hydroxide mechanism. The nitrophenolate in the products can be ionized to generate a bright yellow anion with high absorbance at 348 to 400 nm, as reported in the literature (Armstrong et al., J. Biol. Chem. 1966, 241, 5137-5149). OD340 nm was chosen for detecting hCA II substrate conversion.

Assay working solutions were made as follows:
Assay buffer: 50 mM MOPS, 33 mM Na2SO4, 1 mM EDTA, 0.5 mg/ml BSA, pH 7.5;
Enzyme solution: hCA-II (human, full length) stock solution (1.0 mg/mL in 20 mM HEPES, 50 mM NaCl, pH 7.4), diluted to 2133× final concentration in assay buffer;
4-NPA substrate solution: 4-NPA substrate stock solution (250 mM in DMSO, stored at −20° C.), diluted to 50× final concentration in deionized water.

Test compounds (10 mM stock in DMSO, 100 μL) were obtained in 96-well sample plates (Corning Costar #3655) and diluted to 0.5 mM. Column-wise serial dilutions were made by transferring 20 μL compound solutions to the next column, from column 3 up to 22. After this, 1.2 μL were transferred to 384 well assay plates (Corning Costar #3701). Then 30 μL of 16 nM hCA II solution was added (8 nM final concentration), mixed five times. 30 μL of 4-NPA substrate solution was added (2.5 mM final concentration), mixed five times. Absorbance at 340 nm was then measured immediately as time zero. The assay plates were incubated at room temperature for 1 hour and then measured as time 1 hour (Perkin Elmer EnVision 2103; Filter: Photometric 340; Light intensity 60%; Number of flashes: 10). $IC_{50}$ values and $K_i$ values were calculated from these readouts.

| Ex | ATX IC50 (μM) | CA-II IC50 (μM) |
|---|---|---|
| 1.00 | 0.008 | 0.005 |
| 1.01 | 0.01 | 0.008 |
| 1.02 | 0.006 | 0.01 |
| 1.03 | 0.006 | |
| 1.04 | 0.003 | |
| 1.05 | 0.02 | |
| 1.06 | 0.006 | |
| 1.07 | 0.006 | 0.013 |
| 1.08 | 0.017 | 0.018 |
| 1.09 | 0.01 | 0.01 |
| 2.00 | 0.007 | 0.006 |
| 3.00 | 0.005 | 0.009 |
| 3.01 | 0.007 | 0.006 |
| 3.02 | 0.008 | 0.006 |
| 3.03 | 0.004 | 0.006 |
| 4.00 | 0.006 | 0.095 |
| 4.01 | 0.013 | 0.018 |
| 4.02 | 0.008 | 0.01 |
| 4.03 | 0.011 | 0.013 |
| 5.00 | 0.007 | 0.038 |
| 5.01 | 0.006 | 0.027 |
| 5.02 | 0.004 | 0.015 |
| 5.03 | 0.013 | 0.02 |

Compounds of formula (I) and their pharmaceutically acceptable salts or esters thereof as described herein have $IC_{50}$ values between 0.00001 μM and 1000 μM, particular compounds have $IC_{50}$ values between 0.0005 μM and 500 μM, further particular compounds have $IC_{50}$ values between 0.0005 μM and 50 μM, more particular compounds have $IC_{50}$ values between 0.0005 μM and 5 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; PS-BEMP=polystyrene-bound 2-tert-butylimino-2-diethylamino-1,3-dimethylperhydro-1,3,2-diazaphosphorine; sat.=saturated

Example 1 trans-5-(2-Fluoro-4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester

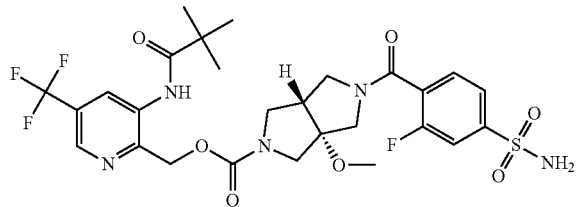 [SMILES: CO[C@]12CN(C(=O)OCc3ncc(C(F)(F)F)cc3NC(=O)C(C)(C)C)C[C@@H]1CN(C(=O)c1ccc(S(N)(=O)=O)cc1F)C2]

To a solution of trans-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester dihydrochloride (intermediate 5; 96 mg, 186 μmol), 4-methylmorpholine (113 mg, 1.11 mmol) and 2-fluoro-4-sulfamoylbenzoic acid (CAS-RN 714968-42-0; 42.8 mg, 186 μmol) in N,N-dimethylformamide (3 mL) was added O-(7-azabenzotriazol-1-yl)-N,N,N',N'-tetramethyluronium hexafluoro-phosphate (70.6 mg, 186 μmol) at room temperature, then after 18 h the reaction mixture was partitioned sat. aq. sodium hydrogen carbonate solution and ethyl acetate/2-methyltetrahydrofuran 4:1. The organic layer was washed with sat. aq. ammonium chloride solution and brine, dried over magnesium sulfate, filtered and evaporated. Chromatography (silica gel; gradient dichloromethane to dichloromethane/methanol/25% aq. ammonia solution 90:10:0.25 afforded the title compound (107 mg, 80%). White solid, MS: 646.2 (M+H)$^+$.

The following examples were produced in analogy to example 1, replacing trans-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester dihydrochloride by the appropriate amine and 2-fluoro-4-sulfamoylbenzoic acid by the appropriate carboxylic acid.

| Ex. | Systematic Name | Amine/Carboxylic acid | MS, m/e |
|---|---|---|---|
| 1.01 | trans-4-[3a-methoxy-2-[3-[4-(trifluoromethoxy)phenyl]propanoyl]-3,4,6,6a-tetrahydro-1H-pyrrolo[3,4-c]pyrrole-5-carbonyl]-3-fluorobenzenesulfonamide | trans-1-(3a-methoxyhexahydropyrrolo[3,4-c]pyrrol-2(1H)-yl)-3-(4-(trifluoromethoxy)phenyl)propan-1-one dihydrochloride (intermediate 6.01)/2-fluoro-4-sulfamoylbenzoic acid (CAS-RN 714968-42-0) | 560.2 (M + H)$^+$ |
| 1.02 | trans-4-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]-3-fluorobenzenesulfonamide | trans-(2-cyclopropyl-6-((tetrahydro-2H-pyran-4-yl)methoxy)pyridin-4-yl)3a-methoxyhexahydropyrrolo[3,4-c]pyrrol-2(1H)-yl)methanone dihydrochloride (intermediate 6)/2-fluoro-4-sulfamoylbenzoic acid (CAS-RN 714968-42-0) | 603.3 (M + H)$^+$ |

| Ex. | Systematic Name | Amine/Carboxylic acid | MS, m/e |
|---|---|---|---|
| 1.03 | trans-5-(4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester | trans-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester dihydrochloride (intermediate 5)/4-sulfamoylbenzoic acid (CAS-RN 138-41-0) | 628.2 (M + H)$^+$ |
| 1.04 | trans-5-(4-sulfamoyl-benzoyl)-3a-fluoro-hexahydro-pyrrolo[3,4-c]pyrrole-2-carboxylic acid 4-trifluoromethoxy-benzyl ester | trans-3a-fluoro-hexahydro-pyrrolo[3,4-c]pyrrole-2-carboxylic acid 4-trifluoromethoxy-benzyl ester (intermediate 4.01)/4-sulfamoylbenzoic acid (CAS-RN 138-41-0) | 530.3 (M − H)$^-$ |
| 1.05 | trans-5-(4-sulfamoyl-benzoyl)-3a-methoxy-hexahydro-pyrrolo[3,4-c]pyrrole-2-carboxylic acid 4-trifluoromethoxy-benzyl ester | trans-3a-fluoro-hexahydro-pyrrolo[3,4-c]pyrrole-2-carboxylic acid 4-trifluoromethoxy-benzyl ester (intermediate 4.01)/4-sulfamoylbenzoic acid (CAS-RN 138-41-0) | 544.2 (M + H)$^+$ |
| 1.06 | trans-3a-methyl-5-(4-sulfamoyl-benzoyl)-hexahydro-pyrrolo[3,4-c]pyrrole-2-carboxylic acid 4-trifluoromethoxy-benzyl ester | trans-3a-methyl-hexahydro-pyrrolo[3,4-c]pyrrole-2-carboxylic acid 4-trifluoromethoxy-benzyl ester hydrochloride (intermediate 4)/4-sulfamoylbenzoic acid (CAS-RN 138-41-0) | 528.2 (M + H)$^+$ |

-continued

| Ex. | Systematic Name | Amine/Carboxylic acid | MS, m/e |
|---|---|---|---|
| 1.07 | trans-5-(5-sulfamoylpyridine-2-carbonyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester | trans-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester dihydrochloride (intermediate 5)/5-sulfamoylpicolinic acid (CAS-RN 1308677-67-9) | 629.2 (M + H)+ |
| 1.08 | trans-6-[3a-methoxy-2-[3-[4-(trifluoromethoxy)phenyl]propanoyl]-3,4,6,6a-tetrahydro-1H-pyrrolo[3,4-c]pyrrole-5-carbonyl]pyridine-3-sulfonamide | trans-1-(3a-methoxyhexahydropyrrolo[3,4-c]pyrrol-2(1H)-yl)-3-(4-(trifluoromethoxy)phenyl)propan-1-one dihydrochloride (interemdiate 6.01)/5-sulfamoylpicolinic acid (CAS-RN 1308677-67-9) | 543.1 (M + H)+ |
| 1.09 | trans-6-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]pyridine-3-sulfonamide | trans-(2-cyclopropyl-6-((tetrahydro-2H-pyran-4-yl)methoxy)pyridin-4-yl)3a-methoxyhexahydropyrrolo[3,4-c]pyrrol-2(1H)-yl)methanone dihydrochloride (intermediate 6)/5-sulfamoylpicolinic acid(CAS-RN 1308677-67-9) | 586.2 (M + H)+ |

Example 2 trans-5-(2-Fluoro-4-sulfamoyl-benzoyl)-3a-fluoro-hexahydro-pyrrolo[3,4-c]pyrrole-2-carboxylic acid 4-trifluoromethoxy-benzyl ester

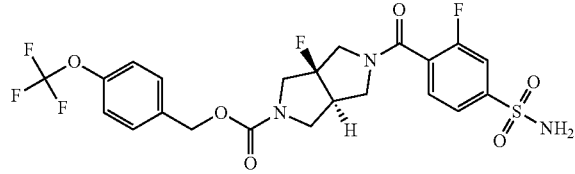 [SMILES: NS(=O)(=O)c1ccc(C(=O)N2C[C@H]3CN(C(=O)OCc4ccc(OC(F)(F)F)cc4)C[C@]3(F)C2)c(F)c1]

To a solution of (4-(trifluoromethoxy)phenyl)methanol (26.1 mg, 136 µmol) in acetonitrile (5 mL) was added 1,1'-carbonyldiimidazole (22 mg, 136 µmol) and the reaction mixture was heated at 50° C. for 2 h, then triethylamine (68.8 mg 680 µmol) and 3-fluoro-4-(trans-3a-fluorooctahydropyrrolo[3,4-c]pyrrole-2-carbonyl)benzenesulfonamide hydrochloride (50 mg, 136 µmol) were added and the reaction mixture was heated at reflux for another 15 h. After cooling the reaction mixture was partitioned between ethyl acetate and sat. aq. sodium hydrogen carbonate solution. The organic layer was washed with sat. aq. ammonium chloride solution and brine, dried over magnesium sulfate, filtered and evaporated. Chromatography (silica gel; gradient dichloromethane to dichloromethane/methanol/25% aq. ammonia solution 90:10:0.25 afforded the title compound (59 mg, 79%). White foam, MS: 550.1 (M+H)⁺.

Example 3 trans-4-[3a-Fluoro-2-[(E)-3-[4-(trifluoromethoxy)phenyl]prop-2-enoyl]-3,4,6,6a-tetrahydro-1H-pyrrolo[3,4-c]pyrrole-5-carbonyl]-3-fluorobenzenesulfonamide

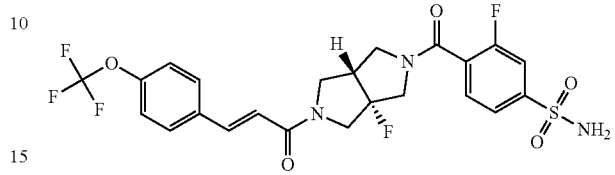

To a solution of 3-fluoro-4-((3aR,6aS)-3a-fluorooctahydropyrrolo[3,4-c]pyrrole-2-carbonyl)benzenesulfonamide hydrochloride (intermediate 9; 50 mg, 122 µmol), 4-methylmorpholine (61.9 mg, 612 µmol) and (E)-3-(4-(trifluoromethoxy)phenyl)acrylic acid (29 mg, 122 µmol) in N,N-dimethylformamide (4 mL) was added O-(7-azabenzotriazol-1-yl)-N,N,N',N'-tetramethyluronium hexafluoro-phosphate (46.5 mg, 122 µmol) at room temperature, then after 18 h the reaction mixture was partitioned between sat. aq. sodium hydrogen carbonate solution and ethyl acetate/2-methyltetrahydrofuran 4:1. The organic layer was washed with sat. aq. ammonium chloride solution and brine, dried over magnesium sulfate filtered and evaporated. Chromatography (silica gel; gradient dichloromethane/methanol/25% aq. ammonia solution 97.5:2.5:0.25 to 95:5:0.25) afforded the title compound (48 mg, 72%). White solid, MS: 546.1 (M+H)⁺.

The following examples were produced in analogy to example 3, replacing 3-fluoro-4-((3aR,6aS)-3a-fluorooctahydropyrrolo[3,4-c]pyrrole-2-carbonyl)benzenesulfonamide hydrochloride by the appropriate amine and (E)-3-(4-(trifluoromethoxy)phenyl)acrylic acid by the appropriate carboxylic acid.

| Ex. | Systematic name | Amine/Carboxylic acid | MS, m/e |
| --- | --- | --- | --- |
| 3.01 | trans-4-[3a-fluoro-2-[2-[4-(trifluoromethoxy)phenoxy]acetyl]-3,4,6,6a-tetrahydro-1H-pyrrolo[3,4-c]pyrrole-5-carbonyl]-3-fluorobenzenesulfonamide | 3-fluoro-4-(trans-3a-fluorooctahydropyrrolo[3,4-c]pyrrole-2-carbonyl)benzenesulfonamide hydrochloride (intermediate 9)/2-(4-(trifluoromethoxy)phenoxy)acetic acid (CAS-RN 72220-50-9) | 548.2 (M + H)⁺ |

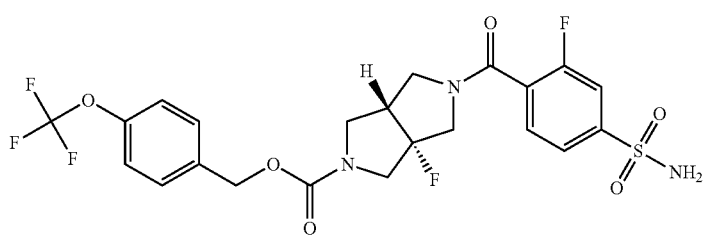

| Ex. | Systematic name | Amine/Carboxylic acid | MS, m/e |
|---|---|---|---|
| 3.02 | trans-4-[5-[2-cyclopropyl-6-(oxan-4-ylmethoxy)pyridine-4-carbonyl]-3a-fluoro-3,4,6,6a-tetrahydro-1H-pyrrolo[3,4-c]pyrrole-2-carbonyl]-3-fluorobenzenesulfonamide | 3-fluoro-4-(trans-3a-fluorooctahydropyrrolo[3,4-c]pyrrole-2-carbonyl)benzenesulfonamide hydrochloride (intermediate 9)/2-cyclopropyl-6-((tetrahydro-2H-pyran-4-yl)methoxy)isonicotinic acid (intermediate 7) | 591.2 (M + H)⁺ |
| 3.03 | trans-4-[3a-fluoro-2-[3-[4-(trifluoromethoxy)phenyl]propanoyl]-3,4,6,6a-tetrahydro-1H-pyrrolo[3,4-c]pyrrole-5-carbonyl]-3-fluorobenzenesulfonamide | 3-fluoro-4-(trans-3a-fluorooctahydropyrrolo[3,4-c]pyrrole-2-carbonyl)benzenesulfonamide hydrochloride (intermediate 9)/3-(4-(trifluoromethoxy)phenyl)propanoic acid | 546.2 (M − H)⁻ |

Examples 4 and 5

(+)-(3aR,6aR)-3a-Methyl-5-(4-sulfamoyl-benzoyl)-hexahydro-pyrrolo[3,4-c]pyrrole-2-carboxylic acid 4-trifluoromethoxy-benzyl ester and (−)-(3aS,6aS)-3a-methyl-5-(4-sulfamoylbenzoyl)-hexahydro-pyrrolo[3,4-c]pyrrole-2-carboxylic acid 4-trifluoromethoxy-benzyl ester Racemic trans-3a-methyl-5-(4-sulfamoyl-benzoyl)-hexahydro-pyrrolo[3,4-c]pyrrole-2-carboxylic acid 4-trifluoromethoxy-benzyl ester (example 1.06; 180 mg, 341 μmol) was separated by preparative HPLC using Chiralpak AD as the stationary phase and heptane/ethanol/ammonium acetate 60:40:0.004 as the eluent. This produced the faster eluting (+)-enantiomer (example 4; 67 mg, 37%; white foam, MS:

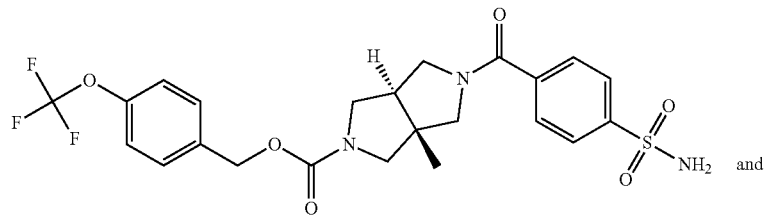

and

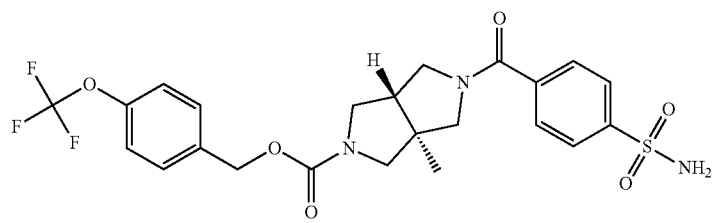

528.2 (M+H)⁺) and the slower eluting (−)-enantiomer (example 5; 63 mg, 35%; white foam, MS: 528.2 (M+H)+).

The following examples were produced in analogy to examples 4 and 5 by chiral HPLC separation of their racemates, using stationary phase and eluent as indicated below.

| Ex. | Systematic Name | Optical rotation sign | Stationary phase; eluent | MS, m/e |
|---|---|---|---|---|
| 4.01 | trans-5-(4-sulfamoyl-benzoyl)-3a-methoxy-hexahydro-pyrrolo[3,4-c]pyrrole-2-carboxylic acid 4- | (−) | Reprosil Chiral-NR; heptane/ethanol/ ammonium acetate 60:40:0.004 | 542.3 (M − H)⁻ |
| 5.01 | trifluoromethoxy-benzyl ester (example 1.05) | (+) | | 542.3 (M − H)⁻ |
| 4.02 | trans-5-(4-sulfamoyl-benzoyl)-3a-fluoro-hexahydro-pyrrolo[3,4-c]pyrrole-2-carboxylic acid 4- | (−) | Reprosil Chiral-NR; heptane/ethanol/ ammonium acetate 70:30:0.003 | 530.2 (M − H)⁻ |
| 5.02 | trifluoromethoxy-benzyl ester (example 1.04) | (+) | | 530.2 (M − H)⁻ |
| 4.03 | trans-5-(4-sulfamoyl-benzoyl)-3a-methoxy-hexahydro-pyrrolo[3,4-c]pyrrole-2-carboxylic acid 3-(2,2-dimethyl-propionylamino)-5- | (−) | Reprosil Chiral-NR; heptane/ethanol 60:40 | 628.3 (M + H)⁺ |
| 5.03 | trifluoromethyl-pyridin-2-ylmethyl ester (example 1.03) | (+) | | 628.3 (M + H)⁺ |

Intermediates

Intermediate 1 trans-tert-Butyl 3a-methylhexahydropyrrolo[3,4-c]pyrrole-2(1H)-carboxylate

Step 1: trans-Dimethyl 1-benzyl-3-methylpyrrolidine-3,4-dicarboxylate

A solution of N-benzyl-1-methoxy-N-((trimethylsilyl)methyl)methanamine (CAS-RN 93102-05-7; 1.74 g, 17.0 mmol) in dichloromethane (5 mL) was added to an ice-cooled mixture of dimethyl 2-methylfumarate (CAS-RN 617-53-8; 1.00 g, 6.32 mmol) and trifluoroacetic acid (79.3 mg, 696 µmol) in dichloromethane (10 mL) at 0-5° C. The resulting yellow solution was allowed to reach room temperature over 20 h, then partitioned between sat. aq. hydrogencarbonate solution and dichloromethane. The organic layer was washed with brine, dried over magnesium sulfate, filtered and evaporated. Chromatography (silica gel; gradient dichloromethane to dichloromethane/methanol/25% aq. ammonia solution 95:5:0.25) afforded the title compound (1.61 g, 87%). Light yellow oil, MS: 292.2 (M+H)⁺.

Step 2: trans-1-tert-Butyl 3,4-dimethyl 3-methylpyrrolidine-1,3,4-tricarboxylate A solution of trans-dimethyl 1-benzyl-3-methylpyrrolidine-3,4-dicarboxylate (1.56 g, 5.35 mmol) and di-tert-butyl dicarbonate (1.29 g, 5.89 mmol) in methanol (20 mL) was stirred at room temperature under a hydrogen atomsphere (1 bar) in the presence of palladium (10% on activated charcoal, 165 mg, 1.55 mmol). After 3 h insoluble material was removed by filtration through diatomaceous earth and the filtrate was concentrated. Chromatography (silica gel; gradient heptane to ethyl acetate/heptane 1:1) afforded the title compound (1.47 g, 91%). Colourless oil, MS: 202.1 (M+H-Me₃COCO)⁺.

Step 3: trans-tert-Butyl 3,4-bis(hydroxymethyl)-3-methylpyrrolidine-carboxylate

A solution of trans-1-tert-butyl 3,4-dimethyl 3-methylpyrrolidine-1,3,4-tricarboxylate (1.47 g, 4.87 mmol) in tetrahydrofuran (12 mL) was cooled to 0° C. and treated with lithium borohydride solution (2 M in tetrahydrofuran, 5.47 mL, 10.9 mmol), then after 30 min the ice bath was removed and the reaction mixture was stirred at room temperature. After 18 h excess reagent was destroyed by slow addition of 1 M aq. hydrochloric acid solution at 0° C. to pH 1. The resulting clear solution was extracted with dichloromethane, the organic layer was washed with water and brine, dried over magnesium sulfate, filtered and evaporated. Chromatography (silica gel, heptane-ethyl acetate gradient) afforded the title compound (1.05 g, 88%). Colourless viscous oil, MS: 190.1 (M+H-isobutene)⁺.

Step 4: trans-tert-Butyl 3-methyl-3,4-bis(((methylsulfonyl)oxy)methyl)pyrrolidine-1-carboxylate Methanesulfonyl chloride (1.41 g, 12.4 mmol) was added dropwise at 0° C. to a clear colourless solution of trans-tert-butyl 3,4-bis(hydroxymethyl)-3-methylpyrrolidine-1-carboxylate (1.01 g, 4.12 mmol) and N,N-diisopropylethylamine (3.19 g, 24.7 mmol) in dichloromethane (10 mL) was cooled to 0° C. After 30 min the reaction mixture was partitioned between sat. aq. ammonium chloride solution and dichloromethane. The organic layer was washed with sat. aq. sodium hydrogencarbonate-solution and brine, dried over magnesium sulfate, filtered and evaporated. Chromatography (silica gel, heptane-ethyl acetate gradient) afforded the title compound (1.53 g, 92%). Yellow viscous oil, MS: 346.1 (M+H-isobutene)⁺.

Step 5: trans-tert-Butyl 5-benzyl-3a-methylhexahydropyrrolo[3,4-c]pyrrole-2(1H)-carboxylate To a solution of trans-tert-butyl 3-methyl-3,4-bis(((methylsulfonyl)oxy)methyl)pyrrolidine-1-carboxylate (1.52 g, 3.79 mmol) in toluene (20 mL) were added triethylamine (1.15 g, 11.4 mmol) and benzylamine (811 mg, 7.57 mmol). The reaction mixture was heated at reflux, then after 20 h another portion of triethylamine (1.15 g, 11.4 mmol) and benzylamine (811 mg, 7.57 mmol) was added, then after another 20 h at reflux the reaction mixture was washed with 1 M aq. sodium hydroxide solution and brine, dried over magnesium sulfate, filtered and evaporated. Chromatography (silica gel, heptane-ethyl acetate gradient) afforded the title compound (875 mg, 73%). Light yellow solid, MS: 317.2 (M+H)⁺.

Step 6: trans-tert-Butyl 3a-methylhexahydropyrrolo[3,4-c]pyrrole-2(1H)-carboxylate A solution of (3aR,6aR)-tert-butyl 5-benzyl-3a-methyl-hexahydropyrrolo[3,4-c]pyrrole-2(1H)-carboxylate (870 mg, 2.75 mmol) in methanol (10 mL) was stirred at room temperature under a hydrogen atmosphere (1 bar) in the presence of palladium (10% on activated charcoal, 146 mg, 1.37 mmol), then after 5 h insoluble material was removed by filtration through diatomaceous earth. The filtrate was evaporated to afford the title compound (640 mg, 93%) containing ca. 10% of methanol. Colourless viscous oil, MS: 227.2 (M+H)$^+$.

Intermediate 2 trans-tert-butyl 3a-fluorohexahydropyrrolo[3,4-c]pyrrole-2(1H)-carboxylate

The title compound was produced in analogy to intermediate 1, replacing dimethyl 2-methylfumarate by diethyl 2-fluorofumarate (CAS-RN 4495-77-6). Colourless viscous oil, MS: 231.2 (M+H)$^+$.

Intermediate 3 trans-tert-Butyl 3a-methoxyhexahydropyrrolo[3,4-c]pyrrole-2(1H)-carboxylate

The title compound was produced in analogy to intermediate 1, replacing dimethyl 2-methylfumarate by dimethyl 2-methoxyfumarate (CAS-RN 2215-05-6). Colourless viscous oil, MS: 243.2 (M+H)$^+$.

Intermediate 4 trans-3a-Methyl-hexahydro-pyrrolo[3,4-c]pyrrole-2-carboxylic acid 4-trifluoromethoxy-benzyl ester hydrochloride

Step 1: trans-2-tert-Butyl 5-(4-(trifluoromethoxy)benzyl) 3a-methyltetrahydropyrrolo[3,4-c]pyrrole-2,5(1H,3H)-dicarboxylate To a solution of (4-(trifluoromethoxy)phenyl)methanol (474 mg, 2.47 mmol) in acetonitrile (20 mL) was added 1,1'-carbonyldiimidazole (413 mg, 2.47 mmol) and the reaction mixture was heated to 50° C., then after 3 h triethylamine (1.25 g, 12.3 mmol) and trans-tert-butyl 3a-methylhexahydropyrrolo[3,4-c]pyrrole-2(1H)-carboxylate (intermediate 1; 621 mg, 2.47 mmol) were added and the reaction mixture was heated at reflux. After 15 h the reaction mixture was partitioned between ethyl acetate sat. aq. sodium hydrogen carbonate solution. The organic layer was washed with aq. sat. ammonium chloride solution and brine, dried over magnesium sulfate, filtered and evaporated. Chromatography (silica gel; gradient dichloromethane to dichloromethane/methanol/25% aq. ammonia solution 95:5:0.25) afforded the title compound (821 mg, 75%). Light yellow oil, MS: 389.2 (M+H-isobutene)$^+$.

Step 2: trans-3a-methyl-hexahydro-pyrrolo[3,4-c]pyrrole-2-carboxylic acid 4-trifluoromethoxy-benzyl ester hydrochloride A solution of trans-2-tert-Butyl 5-(4-(trifluoromethoxy)benzyl) 3a-methyltetrahydropyrrolo[3,4-c]pyrrole-2,5(1H,3H)-dicarboxylate (812 mg, 1.83 mmol) and hydrochloric acid solution (5-6 M in 2-propanol, 10.2 mL, 51.2 mmol) in 2-propanol (5 mL) was stirred for 15 h at room temperature, then concentrated to dryness. The residue was triturated in tert-butyl methyl ether and the precipitate collected by filtration to produce the title compound (662 mg, 95%). White solid, MS: 345.1 (M+H)$^+$.

Intermediate 4.01 trans-3a-Fluoro-hexahydro-pyrrolo[3,4-c]pyrrole-2-carboxylic acid 4-trifluoromethoxy-benzyl ester The title compound was produced in analogy to intermediate 4, replacing trans-tert-butyl 3a-methylhexahydropyrrolo[3,4-c]pyrrole-2(1H)-carboxylate by trans-tert-butyl 3a-fluorohexahydropyrrolo[3,4-c]pyrrole-2(1H)-carboxylate (intermediate 2). White solid, MS: 349.1 (M+H)$^+$.

Intermediate 5 trans-3a-Methoxy-hexahydro-pyrrolo[3,4-c]pyrrole-2-carboxylic acid 3-(2,2-dimethyl-propionylamino)-5-trifluoromethyl-pyridin-2-ylmethyl ester dihydrochloride

Step 1: trans-tert-Butyl 5-(chlorocarbonyl)-3a-methoxyhexahydropyrrolo[3,4-c]pyrrole-2(1H)-carboxylate To a solution of trans-tert-butyl 3a-methoxyhexahydropyrrolo[3,4-c]pyrrole-2(1H)-carboxylate (intermediate 3; 440 mg, 1.82 mmol) and pyridine (646 mg, 8.17 mmol) in dichloromethane (5 mL) was added dropwise a solution of triphosgene (242 mg, 817 μmol) in dichloromethane (4 mL) at 0° C. After 30 min the ice bath was removed, then after 4 h the reaction mixture was partitioned between dichloromethane and 1 M aq. hydrochloric acid solution. The organic layer was washed with water and brine, dried over magnesium sulfate, filtered, and evaporated to afford the title compound (372 mg, 67%) as a light yellow foam.

Step 2: trans-2-tert-Butyl 5-((3-pivalamido-5-(trifluoromethyl)pyridin-2-yl)methyl) 3a-methoxytetrahydropyrrolo[3,4-c]pyrrole-2,5(1H,3H)-dicarboxylate To a solution of trans-tert-butyl 5-(chlorocarbonyl)-3a-methoxyhexahydropyrrolo[3,4-c]pyrrole-2(1H)-carboxylate (370 mg, 1.21 mmol) in acetonitrile (25 mL) was added N-(2-(hydroxymethyl)-5-(trifluoromethyl)pyridin-3-yl) pivalamide (intermediate 8; 335 mg, 1.21 mmol) and PS-BEMP (CAS-RN 1446424-86-7; 1.5 g, 1.21 mmol). The orange suspension was heated at reflux for 21 h, then insoluble material was removed by filtration. To the filtrate was added PS-Trisamine (CAS-RN 1226492-10-9; 315 mg, 1.21 mmol) and the reaction mixture was stirred at room temperature for 18 h, then insoluble material was removed by filtration and the filtrate was evaporated. Chromatography (silica gel; gradient dichloromethane to dichloromethane/methanol/25% aq. ammonia 95:5:0.25) produced the title compound (333 mg, 50%). White foam, MS: 545.3 (M+H)$^+$.

Step 3: trans-3a-Methoxy-hexahydro-pyrrolo[3,4-c]pyrrole-2-carboxylic acid 3-(2,2-dimethyl-propionylamino)-5-trifluoromethyl-pyridin-2-ylmethyl ester dihydrochloride A solution of trans-2-tert-butyl 5-((3-pivalamido-5-(trifluoromethyl)pyridin-2-yl)methyl) 3a-methoxytetrahydropyrrolo[3,4-c]pyrrole-2,5(1H,3H)-dicarboxylate (325 mg, 597

μmol) and hydrochloric acid solution (5-6 M in 2-propanol, 3.34 mL, 16.7 mmol) in 2-propanol (2 mL) was stirred at room temperature for 18 h, then the reaction mixture was concentrated to dryness. The residue was triturated in tert-butyl methyl ether and the precipitate collected by filtration to afford the title compound (291 mg, 94%). White solid, MS: 445.2 (M+H)$^+$.

Intermediate 6 trans-(2-Cyclopropyl-6-((tetrahydro-2H-pyran-4-yl) methoxy)pyridin-4-yl)3a-methoxyhexahydropyrrolo [3,4-c]pyrrol-2(1H)-yl)methanone dihydrochloride Step 1: trans-tert-Butyl 5-(2-cyclopropyl-6-((tetrahydro-2H-pyran-4-yl)methoxy)isonicotinoyl)-3a-methoxyhexahydropyrrolo[3,4-c]pyrrole-2(1H)-carboxylate To a solution of trans-tert-butyl 3a-methoxyhexahydropyrrolo[3,4-c]pyrrole-2(1H)-carboxylate (500 mg, 2.06 mmol) in N,N-dimethylformamide (40 mL) were added 2-cyclopropyl-6-((tetrahydro-2H-pyran-4-yl)methoxy) isonicotinic acid (intermediate 7; 572 mg, 2.06 mmol) and 4-methylmorpholine (1.04 g, 10.3 mmol). The solution was cooled to 0° C., then. O-(7-azabenzotriazol-1-yl)-N,N,N',N'-tetramethyluronium hexafluoro-phosphate (824 mg, 2.17 mmol) was added. The ice bath was removed, then after 96 h the reaction mixture was partitioned between sodium hydrogencarbonate solution and ethyl acetate/2-methyltetrahydrofuran 4:1. The organic layer was washed with sat. aq. ammonium chloride solution and brine, dried over magnesium sulfate, filtered, and evaporated. Chromatography (silica gel; gradient dichloromethane to dichloromethane/methanol/25% aq. ammonia solution 90:10:0.25 afforded the title compound (977 mg; 94%). Yellow viscous oil, MS: 502.3 (M+H)$^+$.

Step 2: trans-(2-Cyclopropyl-6-((tetrahydro-2H-pyran-4-yl)methoxy)pyridin-4-yl)3a-methoxyhexahydropyrrolo[3,4-c]pyrrol-2(1H)-yl)methanone dihydrochloride A solution of trans-tert-butyl 5-(2-cyclopropyl-6-((tetrahydro-2H-pyran-4-yl)methoxy)isonicotinoyl)-3a-methoxyhexahydropyrrolo[3,4-c]pyrrole-2(1H)-carboxylate (977 mg, 1.95 mmol) and hydrochloric acid solution (5-6 M in 2-propanol, 8.57 mL, 42.8 mmol). in 2-propanol (8 mL) was stirred at room temperature for 16 h, then the reaction mixture was concentrated to dryness. The residue was triturated in tert-butyl methyl ether and the precipitate collected by filtration to afford the title compound (858 mg, 88%). White solid, MS: 402.3 (M+H)$^+$.

Intermediate 6.01 trans-1-(3a-methoxyhexahydropyrrolo[3,4-c]pyrrol-2(1H)-yl)-3-(4-(trifluoromethoxy)phenyl)propan-1-one dihydrochloride The title compound was produced in analogy to example 6, replacing 2-cyclopropyl-6-((tetrahydro-2H-pyran-4-yl) methoxy)isonicotinic acid by 3-(4-(trifluoromethoxy)phenyl)propanoic acid. Brown viscous oil, MS: 359.2 (M+H)$^+$.

Intermediate 7

2-Cyclopropyl-6-((tetrahydro-2H-pyran-4-yl) methoxy)isonicotinic acid

Step 1: Methyl 6-cyclopropyl-2-oxo-1,2-dihydropyridine-4-carboxylate

A suspension of 6-cyclopropyl-2-oxo-1,2-dihydropyridine-4-carboxylic acid (CAS-RN 150190-28-6; 400 mg, 2.23 mmol) in methanol (4 mL) and sulfuric acid (12 μL) was added was heated at 70° C. for 48 h, then concentrated in vacuo. The residue was suspended in dichloromethane (10 mL), then insoluble material was removed by filtration and the filtrate evaporated to produce the title compound (427 mg, 99%). Light brown semisolid, MS: 194.1 (M+H)$^+$.

Step 2: Methyl 2-cyclopropyl-6-((tetrahydro-2H-pyran-4-yl)methoxy)isonicotinate

To a stirring suspension of methyl 6-cyclopropyl-2-oxo-1,2-dihydropyridine-4-carboxylate (212 mg, 1.1 mmol) in acetonitrile (5 mL) were added potassium carbonate (455 mg, 3.29 mmol) and 4-(iodomethyl)tetrahydro-2H-pyran (CAS-RN 101691-94-5; 744 mg, 3.29 mmol). The reaction mixture was heated at 80° C. for 16 h and then evaporated in vacuo. The residue was purified by chromatography (silica gel; heptane-ethyl acetate gradient) to produce the title compound (188 mg, 59%). Colourless oil, MS: 292.2 (M+H)$^+$.

Step 3: 2-Cyclopropyl-6-((tetrahydro-2H-pyran-4-yl)methoxy)isonicotinic acid

To a solution of methyl 2-cyclopropyl-6-((tetrahydro-2H-pyran-4-yl)methoxy)isonicotinate (184 mg, 632 μmol) in tetrahydrofuran (2 mL) and water (2 mL) was added lithium hydroxide monohydrate (53.0 mg, 1.26 mmol) and the resulting mixture stirred at room temperature for 16 h. The mixture was partially evaporated in order to remove the tetrahydrofuran. The aqueous phase was partitioned between 1 M aq. hydrochloric acid solution and ethyl acetate. The organic layer was washed with brine, dried over magnesium sulfate, filtered and evaporated to give the title compound (218 mg, quant.). Colourless oil, MS: 276.1 (M–H)$^-$.

Intermediate 8

N-(2-(Hydroxymethyl)-5-(trifluoromethyl)pyridin-3-yl)pivalamide

Step 1: Methyl 3-pivalamido-5-(trifluoromethyl)picolinate

To a brown solution of methyl 3-amino-5-(trifluoromethyl)picolinate (CAS-RN 866775-17-9; 2.00 g, 8.63 mmol) in pyridine (25 mL) was added pivaloyl chloride (2.08 g, 17.3 mmol) at 0° C. After 20 min the ice-bath was removed, then after 5 h the reaction mixture was partitioned between 1 M aq. hydrochloric acid solution and ethyl acetate. The organic layer was washed with water and brine, dried over magnesium sulfate, filtered and evaporated. Chromatography (silica gel; heptante-ethyl acetate gradient) afforded the title compound (2.46 g, 92%). Light yellow solid, MS: 305.1 (M+H)$^+$.

Step 2: N-(2-(Hydroxymethyl)-5-(trifluoromethyl) pyridin-3-yl)pivalamide

To a clear light yellow solution of methyl 3-pivalamido-5-(trifluoromethyl)picolinate (2.45 g, 8.05 mmol) in tetrahydrofuran (60 mL) was added a solution of calcium chloride (1.79 g, 16.1 mmol) in ethanol (60 mL), then sodium borohydride (914 mg, 24.2 mmol) was added in three portions over a period of 30 min. The white suspension was stirred for 90 min at room temperature, then partitioned between water and sat. aq. ammonium chloride solution. The organic layer was washed with brine, dried over magnesium sulfate, filtered, and evaporated. Chromatography (silica gel; heptane-ethyl acetate gradient) afforded the title compound (1.97 g; 89%). Light yellow viscous oil, MS: 277.1 (M+H)$^+$.

Intermediate 9

3-Fluoro-4-(trans-3a-fluorooctahydropyrrolo[3,4-c]pyrrole-2-carbonyl)benzenesulfonamide hydrochloride Step 1: trans-tert-butyl 3a-fluoro-5-(2-fluoro-4-sulfamoylbenzoyl)hexahydropyrrolo[3,4-c]pyrrole-2(1H)-carboxylate The title compound was produced in analogy to intermediate 6, step 1, replacing trans-tert-butyl 3a-methoxyhexahydropyrrolo[3,4-c]pyrrole-2(1H)-carboxylate by trans-tert-butyl 3a-fluorohexahydropyrrolo[3,4-c]pyrrole-2(1H)-carboxylate and 2-cyclopropyl-6-((tetrahydro-2H-pyran-4-yl)methoxy)isonicotinic acid by 2-fluoro-4-sulfamoylbenzoic acid (CAS-RN 714968-42-0). Light yellow foam, MS: 432.2 (M+H)$^+$.

Step 2: 3-Fluoro-4-(trans-3a-fluorooctahydropyrrolo[3,4-c]pyrrole-2-carbonyl)benzenesulfonamide hydrochloride The title compound was produced in analogy to intermediate 6, step 2 from trans-tert-butyl 3a-fluoro-5-(2-fluoro-4-sulfamoylbenzoyl)hexahydropyrrolo[3,4-c]pyrrole-2(1H)-carboxylate. White solid, MS: 332.0 (M+H)$^+$.

Example A

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:
1. A method, wherein the method is for the treatment of an ocular condition in a mammal, the method comprising administering to the mammal a compound, wherein the compound is of formula (I):

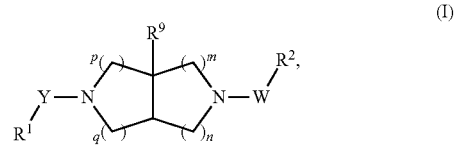

or a pharmaceutically acceptable salt thereof, wherein:
$R^1$ is substituted phenyl, substituted phenyl-$C_{1-6}$-alkyl, substituted phenoxy-$C_{1-6}$-alkyl, substituted phenyl-$C_{2-6}$-alkenyl, substituted phenyl-$C_{2-6}$-alkynyl, substituted pyridinyl, substituted pyridinyl-$C_{1-6}$-alkyl, substituted pyridinyl-$C_{2-6}$-alkenyl, substituted pyridinyl-$C_{2-6}$-alkynyl, substituted thiophenyl, substituted thiophenyl-$C_{1-6}$-alkyl, substituted thiophenyl-$C_{2-6}$-alkenyl or substituted thiophenyl-$C_{2-6}$-alkynyl, wherein substituted phenyl, substituted phenyl-$C_{1-6}$-alkyl, substituted phenoxy-$C_{1-6}$-alkyl, substituted phenyl-$C_{2-6}$-alkenyl, substituted phenyl-$C_{2-6}$-alkynyl, substituted pyridinyl, substituted pyridinyl-$C_{1-6}$-alkyl, substituted pyridinyl-$C_{2-6}$-alkenyl, substituted pyridinyl-$C_{2-6}$-alkynyl, substituted thiophenyl, substituted thiophenyl-$C_{1-6}$-alkyl, substituted thiophenyl-$C_{2-6}$-alkenyl and substituted thiophenyl-$C_{2-6}$-alkynyl are substituted by $R^3$, $R^4$ and $R^5$;
Y is —OC(O)— or —C(O)—;
W is —C(O)—, —S(O)$_2$— or —CR$^6$R$^7$—;
$R^2$ is substituted phenyl, substituted pyridinyl or substituted thiophenyl, wherein substituted phenyl, substituted pyridinyl and substituted thiophenyl are substituted by $R^6$, $R^7$ and $R^8$;
$R^3$ is halogen, hydroxy, cyano, $C_{1-6}$-alkyl, $C_{1-6}$-alkoxy, $C_{1-6}$-alkoxy-$C_{1-6}$-alkyl, halo-$C_{1-6}$-alkoxy, halo-$C_{1-6}$-alkyl, hydroxy-$C_{1-6}$-alkyl, $C_{3-8}$-cycloalkyl, $C_{3-8}$-cycloalkyl-$C_{1-6}$-alkyl, $C_{3-8}$-cycloalkyl-$C_{1-6}$-alkoxy, $C_{3-8}$-cycloalkoxy, $C_{3-8}$-cycloalkoxy-$C_{1-6}$-alkyl, $C_{1-6}$-alkylamino, $C_{1-6}$-alkylcarbonylamino, $C_{3-8}$-cycloalkylcarbonylamino, $C_{1-6}$-alkyltetrazolyl, $C_{1-6}$-alkyltetrazolyl-$C_{1-6}$-alkyl or heterocycloalkyl-$C_{1-6}$-alkoxy;
$R^4$ and $R^5$ are independently selected from H, halogen, hydroxy, cyano, $C_{1-6}$-alkyl, $C_{1-6}$-alkoxy, $C_{1-6}$-alkoxy-$C_{1-6}$-alkyl, halo-$C_{1-6}$-alkoxy, halo-$C_{1-6}$-alkyl, hydroxy-$C_{1-6}$-alkyl, $C_{3-8}$-cycloalkyl, $C_{3-8}$-cycloalkyl-$C_{1-6}$-alkyl, $C_{3-8}$-cycloalkyl-$C_{1-6}$-alkoxy, $C_{3-8}$-cycloalkoxy, $C_{3-8}$-cycloalkoxy-$C_{1-6}$-alkyl, $C_{1-6}$-alkylcarbonylamino, $C_{3-8}$-cycloalkylcarbonylamino, $C_{1-6}$-alkyltetrazolyl, $C_{1-6}$-alkyltetrazolyl-$C_{1-6}$-alkyl and heterocycloalkyl-$C_{1-6}$-alkoxy;
$R^6$ is aminosulfonyl;

R⁷ and R⁸ are independently selected from H, halogen, hydroxy, cyano, $C_{1-6}$-alkyl, $C_{1-6}$-alkoxy, $C_{1-6}$-alkoxy-$C_{1-6}$-alkyl, halo-$C_{1-6}$-alkoxy, halo-$C_{1-6}$-alkyl, hydroxy-$C_{1-6}$-alkyl, $C_{3-8}$-cycloalkyl, $C_{3-8}$-cycloalkyl-$C_{1-6}$-alkyl, $C_{3-8}$-cycloalkyl-$C_{1-6}$-alkoxy, $C_{3-8}$-cycloalkoxy and $C_{3-8}$-cycloalkoxy-$C_{1-6}$-alkyl;

$R^9$ is $C_{1-6}$-alkyl, $C_{1-6}$-alkoxy or halogen; and m, n, p and q are each 1.

2. The method of claim 1, wherein:

$R^1$ is substituted phenyl-$C_{1-6}$-alkyl, substituted phenoxy-$C_{1-6}$-alkyl, substituted phenyl-$C_{2-6}$-alkenyl, substituted pyridinyl or substituted pyridinyl-$C_{1-6}$-alkyl, wherein substituted phenyl-$C_{1-6}$-alkyl, substituted phenoxy-$C_{1-6}$-alkyl, substituted phenyl-$C_{2-6}$-alkenyl, substituted pyridinyl and substituted pyridinyl-$C_{1-6}$-alkyl are substituted by $R^3$, $R^4$ and $R^5$;

Y is —OC(O)— or —C(O)—;

W is —C(O)—;

$R^2$ is substituted phenyl or substituted pyridinyl, wherein substituted phenyl and substituted pyridinyl are substituted by $R^6$, $R^7$ and $R^8$;

$R^3$ is halo-$C_{1-6}$-alkoxy, $C_{1-6}$-alkylcarbonylamino or tetrahydropyranyl-$C_{1-6}$-alkoxy;

$R^4$ is H, $C_{1-6}$-alkyl or $C_{3-8}$-cycloalkyl;

$R^5$ is H;

$R^6$ is aminosulfonyl;

$R^7$ and $R^8$ are independently selected from H and halogen;

$R^9$ is $C_{1-6}$-alkyl, $C_{1-6}$-alkoxy or halogen; and m, n, p and q are 1.

3. The method of claim 1, wherein $R^1$ is substituted phenyl-$C_{1-6}$-alkyl, substituted phenoxy-$C_{1-6}$-alkyl, substituted phenyl-$C_{2-6}$-alkenyl, substituted pyridinyl or substituted pyridinyl-$C_{1-6}$-alkyl, wherein substituted phenyl-$C_{1-6}$-alkyl, substituted phenoxy-$C_{1-6}$-alkyl, substituted phenyl-$C_{2-6}$-alkenyl, substituted pyridinyl and substituted pyridinyl-$C_{1-6}$-alkyl are substituted by $R^3$, $R^4$ and $R^5$.

4. The method of claim 1, wherein $R^1$ is substituted pyridinyl or substituted pyridinyl-$C_{1-6}$-alkyl, wherein substituted pyridinyl and substituted pyridinyl-$C_{1-6}$-alkyl are substituted by $R^3$, $R^4$ and $R^5$.

5. The method of claim 1, wherein Y is —C(O)—.

6. The method of claim 1, wherein $R^2$ is substituted phenyl or substituted pyridinyl, wherein the substituted phenyl or substituted pyridinyl are substituted by $R^6$, $R^7$ and $R^8$.

7. The method of claim 1, wherein $R^3$ is halo-$C_{1-6}$-alkoxy, $C_{1-6}$-alkylcarbonylamino or tetrahydropyranyl-$C_{1-6}$-alkoxy.

8. The method of claim 1, wherein $R^3$ is tetrahydropyranyl-$C_{1-6}$-alkoxy.

9. The method of claim 1, wherein $R^4$ is H, $C_{1-6}$-alkyl or $C_{3-8}$-cycloalkyl.

10. The method of claim 1, wherein $R^4$ is $C_{3-8}$-cycloalkyl.

11. The method of claim 1, wherein $R^5$ is H.

12. The method of claim 1, wherein $R^7$ and $R^8$ are independently selected from H and halogen.

13. The method of claim 1, wherein $R^7$ is H or halogen.

14. The method of claim 1, wherein $R^8$ is H.

15. The method of claim 1, wherein $R^9$ is halogen or $C_{1-6}$-alkoxy.

16. The method of claim 1, wherein:

$R^1$ is substituted pyridinyl or substituted pyridinyl-$C_{1-6}$-alkyl, wherein substituted pyridinyl and substituted pyridinyl-$C_{1-6}$-alkyl are substituted by $R^3$, $R^4$ and $R^5$;

Y is —C(O)—;

W is —C(O)—;

$R^2$ is substituted phenyl or substituted pyridinyl, wherein substituted phenyl and substituted pyridinyl are substituted by $R^6$, $R^7$ and $R^8$;

$R^3$ is tetrahydropyranyl-$C_{1-6}$-alkoxy;

$R^4$ is $C_{3-8}$-cycloalkyl;

$R^5$ is H;

$R^6$ is aminosulfonyl;

$R^7$ is H or halogen;

$R^8$ is H;

$R^9$ is halogen or $C_{1-6}$-alkoxy; and m, n, p and q are 1.

17. The method of claim 1, wherein:

$R^1$ is substituted phenyl-$C_{1-6}$-alkyl, substituted phenoxy-$C_{1-6}$-alkyl, substituted phenyl-$C_{2-6}$-alkenyl, substituted pyridinyl or substituted pyridinyl-$C_{1-6}$-alkyl, wherein substituted phenyl-$C_{1-6}$-alkyl, substituted phenoxy-$C_{1-6}$-alkyl, substituted phenyl-$C_{2-6}$-alkenyl, substituted pyridinyl and substituted pyridinyl-$C_{1-6}$-alkyl are substituted by $R^3$, $R^4$ and $R^5$;

Y is —OC(O)— or —C(O)—;

W is —C(O)—;

$R^2$ is substituted phenyl or substituted pyridinyl, wherein substituted phenyl and substituted pyridinyl are substituted by $R^6$, $R^7$ and $R^8$;

$R^3$ is halo-$C_{1-6}$-alkoxy, $C_{1-6}$-alkylcarbonylamino or tetrahydropyranyl-$C_{1-6}$-alkoxy;

$R^4$ is H, $C_{1-6}$-alkyl or $C_{3-8}$-cycloalkyl;

$R^5$ is H;

$R^7$ and $R^8$ are independently selected from H and halogen;

$R^9$ is $C_{1-6}$-alkyl, $C_{1-6}$-alkoxy or halogen; and m, n, p and q are 1.

18. The method of claim 1, wherein:

$R^1$ is substituted pyridinyl or substituted pyridinyl-$C_{1-6}$-alkyl, wherein substituted pyridinyl and substituted pyridinyl-$C_{1-6}$-alkyl are substituted by $R^3$, $R^4$ and $R^5$;

Y is —C(O)—;

W is —C(O)—;

$R^2$ is substituted phenyl or substituted pyridinyl, wherein substituted phenyl and substituted pyridinyl are substituted by $R^6$, $R^7$ and $R^8$;

$R^3$ is tetrahydropyranyl-$C_{1-6}$-alkoxy;

$R^4$ is $C_{3-8}$-cycloalkyl;

$R^5$ is H;

$R^7$ is H or halogen;

$R^8$ is H;

$R^9$ is halogen or $C_{1-6}$-alkoxy; and m, n, p and q are 1;

or a pharmaceutically acceptable salt thereof.

19. The method of claim 1, wherein the compound is selected from the group consisting of:

trans-5-(2-fluoro-4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;

trans-4-[3a-methoxy-2-[3-[4-(trifluoromethoxy)phenyl]propanoyl]-3,4,6,6a-tetrahydro-1H-pyrrolo[3,4-c]pyrrole-5-carbonyl]-3-fluorobenzenesulfonamide;

trans-4-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]-3-fluorobenzenesulfonamide;

trans-5-(4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;

trans-5-(4-sulfamoyl-benzoyl)-3a-fluoro-hexahydro-pyrrolo[3,4-c]pyrrole-2-carboxylic acid 4-trifluoromethoxy-benzyl ester;

trans-5-(4-sulfamoyl-benzoyl)-3a-methoxy-hexahydro-pyrrolo[3,4-c]pyrrole-2-carboxylic acid 4-trifluoromethoxy-benzyl ester;

trans-3a-methyl-5-(4-sulfamoyl-benzoyl)-hexahydro-pyrrolo[3,4-c]pyrrole-2-carboxylic acid 4-trifluoromethoxy-benzyl ester;

trans-5-(5-sulfamoylpyridine-2-carbonyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;

trans-6-[3a-methoxy-2-[3-[4-(trifluoromethoxy)phenyl]propanoyl]-3,4,6,6a-tetrahydro-1H-pyrrolo[3,4-c]pyrrole-5-carbonyl]pyridine-3-sulfonamide;

trans-6-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]pyridine-3-sulfonamide;

trans-5-(2-fluoro-4-sulfamoyl-benzoyl)-3a-fluoro-hexahydro-pyrrolo[3,4-c]pyrrole-2-carboxylic acid 4-trifluoromethoxy-benzyl ester;

trans-4-[3a-fluoro-2-[(E)-3-[4-(trifluoromethoxy)phenyl]prop-2-enoyl]-3,4,6,6a-tetrahydro-1H-pyrrolo[3,4-c]pyrrole-5-carbonyl]-3-fluorobenzenesulfonamide;

trans-4-[3a-fluoro-2-[2-[4-(trifluoromethoxy)phenoxy]acetyl]-3,4,6,6a-tetrahydro-1H-pyrrolo[3,4-c]pyrrole-5-carbonyl]-3-fluorobenzenesulfonamide;

trans-4-[5-[2-cyclopropyl-6-(oxan-4-ylmethoxy)pyridine-4-carbonyl]-3a-fluoro-3,4,6,6a-tetrahydro-1H-pyrrolo[3,4-c]pyrrole-2-carbonyl]-3-fluorobenzenesulfonamide;

trans-4-[3a-fluoro-2-[3-[4-(trifluoromethoxy)phenyl]propanoyl]-3,4,6,6a-tetrahydro-1H-pyrrolo[3,4-c]pyrrole-5-carbonyl]-3-fluorobenzenesulfonamide;

(+)-(3aR,6aR)-3a-methyl-5-(4-sulfamoyl-benzoyl)-hexahydro-pyrrolo[3,4-c]pyrrole-2-carboxylic acid 4-trifluoromethoxy-benzyl ester;

(−)-trans-5-(4-sulfamoyl-benzoyl)-3a-methoxy-hexahydro-pyrrolo[3,4-c]pyrrole-2-carboxylic acid 4-trifluoromethoxy-benzyl ester;

(−)-trans-5-(4-sulfamoyl-benzoyl)-3a-fluoro-hexahydro-pyrrolo[3,4-c]pyrrole-2-carboxylic acid 4-trifluoromethoxy-benzyl ester;

(−)-trans-5-(4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;

(−)-(3aS,6aS)-3a-methyl-5-(4-sulfamoylbenzoyl)-hexahydro-pyrrolo[3,4-c]pyrrole-2-carboxylic acid 4-trifluoromethoxy-benzyl ester;

(+)-trans-5-(4-sulfamoyl-benzoyl)-3a-methoxy-hexahydro-pyrrolo[3,4-c]pyrrole-2-carboxylic acid 4-trifluoromethoxy-benzyl ester;

(+)-trans-5-(4-sulfamoyl-benzoyl)-3a-fluoro-hexahydro-pyrrolo[3,4-c]pyrrole-2-carboxylic acid 4-trifluoromethoxy-benzyl ester; and (+)-trans-5-(4-sulfamoyl-benzoyl)-3a-methoxy-hexahydro-pyrrolo[3,4-c]pyrrole-2-carboxylic acid 3-(2,2-dimethyl-propionylamino)-5-trifluoromethyl-pyridin-2-ylmethyl ester;

or is a pharmaceutically acceptable salt thereof.

20. The method of claim 1, wherein the compound is selected from the group consisting of:

trans-4-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]-3-fluorobenzenesulfonamide;

trans-6-[5-[2-cyclopropyl-6-(oxan-4-ylmethoxy)pyridine-4-carbonyl]-3a-methoxy-3,4,6,6a-tetrahydro-1H-pyrrolo[3,4-c]pyrrole-2-carbonyl]pyridine-3-sulfonamide; and trans-4-[5-[2-cyclopropyl-6-(oxan-4-ylmethoxy)pyridine-4-carbonyl]-3a-fluoro-3,4,6,6a-tetrahydro-1H-pyrrolo[3,4-c]pyrrole-2-carbonyl]-3-fluorobenzenesulfonamide;

or is pharmaceutically acceptable salt thereof.

21. The method of claim 1, wherein the ocular condition is proliferative retinopathy, non-proliferative diabetic retinopathy, dry age-related macular degeneration, wet age-related macular degeneration, macular edema, central arterial occlusion, central venous occlusion, traumatic injury, or glaucoma.

22. The method of claim 19, wherein the ocular condition is proliferative retinopathy, non-proliferative diabetic retinopathy, dry age-related macular degeneration, wet age-related macular degeneration, macular edema, central arterial occlusion, central venous occlusion, traumatic injury, or glaucoma.

23. The method of claim 20, wherein the ocular condition is proliferative retinopathy, non-proliferative diabetic retinopathy, dry age-related macular degeneration, wet age-related macular degeneration, macular edema, central arterial occlusion, central venous occlusion, traumatic injury, or glaucoma.

* * * * *